(12) United States Patent
Lihme et al.

(10) Patent No.: US 6,919,436 B2
(45) Date of Patent: Jul. 19, 2005

(54) ISOLATION OF PROTEINS

(75) Inventors: Allan Otto Fog Lihme, Birkerod (DK); Marie Bendix Hansen, Frederiksberg (DK)

(73) Assignee: Upfront Chromatography A/S, Copenhagen (DK)

(*) Notice: Subject to any disclaimer, the term of this patent is extended or adjusted under 35 U.S.C. 154(b) by 0 days.

(21) Appl. No.: 10/268,667

(22) Filed: Oct. 11, 2002

(65) Prior Publication Data

US 2003/0187227 A1 Oct. 2, 2003

Related U.S. Application Data

(62) Division of application No. 09/147,668, filed as application No. PCT/DK97/00359 on Sep. 1, 1997, now Pat. No. 6,498,236.

(30) Foreign Application Priority Data

Aug. 30, 1996 (DK) .......................................... 1996 0932

(51) Int. Cl.[7] .......................... B01D 15/00; B01J 20/32; C07K 1/22
(52) U.S. Cl. ....................................... 530/413; 530/417
(58) Field of Search .............................. 530/364, 366, 530/368, 369, 412, 413, 415, 416, 417; 502/402

(56) References Cited

U.S. PATENT DOCUMENTS

| | | | | |
|---|---|---|---|---|
| 4,043,997 A | * | 8/1977 | Schroeder | 530/364 |
| 4,066,505 A | * | 1/1978 | Schneider | 435/178 |
| 4,168,300 A | * | 9/1979 | Andersson et al. | 530/380 |
| 4,981,961 A | | 1/1991 | Ngo | 530/809 |
| 5,019,269 A | | 5/1991 | Letourner et al. | 530/413 |
| 5,502,022 A | | 3/1996 | Schwarz et al. | 530/412 |
| 6,498,236 B1 | * | 12/2002 | Lihme et al. | 530/387.1 |

FOREIGN PATENT DOCUMENTS

| | | |
|---|---|---|
| EP | 165912 | 12/1985 |
| EP | 168363 | 1/1986 |
| EP | 261162 | 8/1986 |
| EP | 197521 | 10/1986 |
| EP | 245222 | 11/1987 |
| WO | 89/08257 | 9/1989 |
| WO | 92/16292 | 10/1992 |
| WO | 95/31279 | 11/1995 |
| WO | 95/33557 | 12/1995 |
| WO | 96/00735 | 1/1996 |
| WO | 96/09116 | 3/1996 |
| WO | WO 97/10887 A1 * | 3/1997 |

OTHER PUBLICATIONS

Harris et al, eds. Protein purification methods, a practical approach. Oxford: IRL Press (1989), pp. 208–211.*
Knudsen et al. "*Sulfone–Aromatic Ligands for Thiophilic Adsorption Chromatography: Purification of Human and Mouse Immunoglobulins,*" Anal. Biochem. 201, pp. 170–177 (1992).
Porath et al. "*Thiophilic Adsorption—A New Method for Protein Fractionation,*" FEBS Letters, 185: 306–310 (1985).

* cited by examiner

*Primary Examiner*—Jeffrey Edwin Russel
(74) *Attorney, Agent, or Firm*—Foley & Lardner LLP

(57) ABSTRACT

The present invention relates to a novel method for the isolation or purification of immunoglobulins (a special class of proteins) from a solution containing immunoglobulins, e.g. hybridoma cell culture supernatants, animal plasma or sera, or colostrum. The method includes the use of a minimum of salts, such as lyotropic salts, in the binding process and preferably also the use of small amounts of organic solvents in the elution process. The solid phase matrices, preferably epichlorohydrin activiated agarose matricees, are functionalised with mono- or bicyclic aromatic or heteroaromatic ligands (molecular weight: at the most 500 Dalton) which, preferably, comprises an acidic substituent, e.g. a carboxylic acid. The matrices utilised show excellent properties in a "Standard Immunoglobulin Binding Test" and in a "Monoclonal Antibody Array Binding Test" with respect to binding efficiency and purity, and are stable in 1M NaOH.

17 Claims, No Drawings

ISOLATION OF PROTEINS

This application is a Division of application Ser. No. 09/147,668 filed Mar. 19, 1999, which issued as U.S. Pat. No. 6,498,236 and which is a National Phase Application of PCT Application Serial No. PCT/DK97/00359 filed Sep. 1, 1997, which claims priority to Denmark application Ser. No. 0932/96 filed Aug. 30, 1996.

FIELD OF THE INVENTION

The present invention relates to a method for isolation or purification of immunoglobulins from various raw materials and solid phase matrices therefor.

BACKGROUND OF THE INVENTION

Immunoglobulins or antibodies-constitute a very important class of proteins which are present in various body fluids of mammals, birds and fish functioning as protective agents of the animal against substances, bacteria and virus challenging the animal. Immunoglobulins are typically present in animal blood, milk, and saliva as well as other body fluids and secretions.

The biological activity, which the immunoglobulins possess, is today exploited in a range of different applications in the human and veterinary diagnostic, health care and therapeutic sector.

Diagnostics

Antibodies have for many years been applied as an important analytic tool in connection with detection and quantification of a large variety of substances of relevance in the diagnosis of diseases and are increasingly important in areas such as quality control of food products, environmental control, drugs of abuse, and monitoring and control of industrial processes.

For these purposes, the desired antibodies can be produced by hyper-immunisation of suitable host animals, such as rabbits and sheep, or, alternatively, by producing monoclonal antibodies in hybridoma cell cultures.

Following the primary production of the antibodies in either a host animal or in cell culture, the antibody is typically isolated from the bulk of other substances in the raw material by some sort of isolation process. This is necessary in order to avoid interference from these other substances with the antibody activity in the analytical application.

Health Care and Therapeutic Applications

Passive immunisation by intramuscularly injection of immunoglobulin concentrates is a well-known application for temporary protection against infectious diseases, which is typically applied when people are travelling from one part of the world to the other. The success of this kind of treatment on humans is now being followed up in the veterinary field where passive immunisation of new born cattle, horses, pigs and chickens are being applied and developed to enhance the survival rate of these animals during their first weeks of live. An important issue in this field is of course the cost of such a treatment, which to a high degree depends on the cost of producing the immunoglobulin concentrate.

Isolates of animal immunoglobulins, e.g. from bovine milk, are also under investigation as an oral health care or even therapeutic product to avoid or treat gastrointestinal infections, e.g. in AIDS patients. For such applications both the degree of purity of the product as well as the cost is of major importance.

A more sophisticated application of antibodies for therapeutic use is based on so called "drug-targeting" where very potent drugs are covalently linked to antibodies with specific binding affinities towards specific cells in the human organism, e.g. cancer cells. This technique ensures that the drug is concentrated on the diseased cells giving maximal effect of the drug without the severe side-effects that frequently occurs when using chemotherapy. For such purposes the antibodies have to be very carefully controlled and of high purity, and the typical way of performing the primary production are either by producing monoclonal antibodies in hybridoma cell culture or by fermenting genetically engineered bacteria, e.g. *E.coli.*

Isolation of Immunoglobulins

All the above mentioned applications of immunoglobulins requires some sort of isolation of the antibody from the crude raw material, but each kind of application has its own very varying demands with respect to the final purity and allowable cost of the antibody product.

Generally, there exists a very broad range of different methods available for isolation of immunoglobulins giving a very broad range of final purities, yields and cost of the product.

Traditional methods for isolation of immunoglobulins are based on selective reversible precipitation of the protein fraction comprising the immunoglobulins while leaving other groups of proteins in solution. Typical precipitation agents being ethanol, polyethylene glycol, lyotropic (anti-chaotropic) salts such as ammonium sulfate and potassium phosphate, and caprylic acid.

Typically, these precipitation methods are giving very impure products while at the same time being time consuming and laborious. Furthermore, the addition of the precipitating agent to the raw material makes it difficult to use the supernatant for other purposes and creates a disposal problem. This is particularly relevant when speaking of large scale purification of immunoglobulins from, e.g., whey and plasma.

Ion exchange chromatography is another well known method of protein fractionation frequently used for isolation of immunoglobulins. However, this method is not generally applicable because of the restraints in ionic strength and pH necessary to ensure efficient binding of the antibody together with the varying isoelectric points of different immunoglobulins.

Protein A and Protein G affinity chromatography are very popular and widespread methods for isolation and purification of immunoglobulins, particularly for isolation of monoclonal antibodies, mainly due to the ease of use and the high purity obtained. Although being popular it is however recognised that Protein A and Protein G poses several problems to the user among which are: very high cost, variable binding efficiency of different monoclonal antibodies (particularly mouse $IgG_1$), leakage of Protein A/Protein G into the product, and low stability of the matrix in typical cleaning solutions, e.g. 1 M sodium hydroxide. Each of these drawbacks have its specific consequence in the individual application, ranging from insignificant to very serious and prohibitive consequences.

Hydrophobic chromatography is also a method widely described for isolation of immunoglobulins, e.g. in "Application Note 210, BioProcess Media" published by Pharmacia LKB Biotechnology, 1991. In this reference a state of the art product "Phenyl Sepharose High Performance" is described for the purpose of purifying monoclonal antibodies from cell culture supernatants. As with other hydrophobic matrices employed so far it is necessary to add lyotropic salts to the raw material to make the immunoglobulin bind efficiently. The bound antibody is released from the matrix by lowering the concentration of lyotropic salt in a continuous or stepwise gradient. It is recommended to combine the hydrophobic chromatography with a further step if highly pure product is the object.

The disadvantage of this procedure is the necessity to add lyotropic salt to the raw material as this gives a disposal problem and thereby increased cost to the large scale user. For other raw materials than cell culture supernatants such as whey, plasma, and egg yolk the addition of lyotropic salts to the raw materials would in many instances be prohibitive in large scale applications as the salt would prevent any economically feasible use of the immunoglobulin depleted raw material in combination with the problem of disposing several thousand liters of waste.

Thiophilic adsorption chromatography was introduced by J. Porath in 1985 (J. Porath et al; FEBS Letters, vol. 185, p.306, 1985) as a new chromatographic adsorption principle for isolation of immunoglobulins. In this paper, it is described how divinyl sulfone activated agarose coupled with various ligands comprising a free mercapto-group show specific binding of immunoglobulins in the presence of 0.5 M potassium sulfate, i.e. a lyotropic salt. It was postulated that the sulfone group, from the vinyl sulfone spacer, and the resulting thio-ether in the ligand was a structural necessity to obtain the described specificity and capacity for binding of antibodies. It was however later shown that the thio-ether could be replaced by nitrogen or oxygen if the ligand further comprised an aromatic radical (K. L. Knudsen et al, Analytical Biochemistry, vol 201, p. 170, 1992).

Although the matrices described for thiophilic chromatography generally show good performance, they also have a major disadvantage in that it is needed to add lyotropic salts to the raw material to ensure efficient binding of the immunoglobulin, which is a problem for the reasons discussed above.

Other thiophilic ligands coupled to epoxy activated agarose have been disclosed in (J. Porath et.al., Makromol. Chem., Makromol. Symp., vol. 17, p.359, 1988) and (A. Schwarz et.al., Journal of Chromatography B, vol. 664, pp. 83–88, 1995), e.g. 2-mercaptopyridine, 2-mercaptopyrimidine, and 2-mercaptothiazoline. However, all these affinity matrices still have inadequate affinity constants to ensure an efficient binding of the antibody without added lyotropic salts.

Binding and Isolation of Proteins and other Biomolecules

WO 96/00735 and WO 96/09116 disclose resins (matrices) for purifying proteins and peptides which resins are characterised by the fact that they contain ionizable ligands and/or functionalities which are uncharged at the pH of binding the target protein or peptide, thereby facilitating hydrophobic interactions, and charged at the pH of desorption, thereby disrupting the established hydrophobic interaction between the resin and the target protein or peptide. WO 96/00735 mentions the possibility of coupling 2-mercaptobenzimidazole to epoxy-activated Sepharose 6 B. The actual ligand concentration is not disclosed, however the coupling was performed with an epoxy-activated Sepharose wherein the content of epoxy-groups is disclosed to be in the range of 1.02–1.28 mmol/g dry matter.

WO 92/16292 discloses a number of different ligands coupled to divinyl sulfone activated agarose and the use of the resulting solid phase matrices for thiophilic adsorption of proteins, preferably immunoglobulins. Specifically is mentioned solid phase matrices comprising 4-amino-benzoic acid as a ligand on a divinyl sulfone activated agarose. The adsorption of proteins, preferably immunoglobulins in WO 92/16292, is performed at high concentrations of lyotropic salts i.e. with an ionic strength of on or above 2.25.

BRIEF DESCRIPTION OF THE INVENTION

It has now surprisingly been found that several types of aromatic or heteroaromatic substances linked to a solid phase matrix can be utilised in a novel method for the isolation and/or purification of immunoglobulins of different kinds from widely different raw materials with high efficiency and with special advantages with respect to the use of little or no salts, especially lyotropic salts, in the binding process and with respect to the ability to bind a wide range of immunoglobulins. Furthermore, these matrices have special advantages with respect to stability in NaOH, which is especially relevant when the solid phase matrices are to be regenerated after use.

Thus, an object of the present invention is to provide a method for the isolation of immunoglobulins from a solution containing one or more immunoglobulins, comprising the following operations:

a) contacting a solution containing one or more immunoglobulins and having a pH in the range of 2.0 to 10.0 and a total salt content corresponding to a ionic strength of at the most 2.0 with a solid phase matrix of the general formula $$M\text{-}SP1\text{-}L,$$

wherein M designates the matrix backbone, SP1 designates a spacer, and L designates a ligand comprising a mono- or bicyclic optionally substituted aromatic or heteroaromatic moiety, whereby at least a part of the immunoglobulins becomes bound to the solid phase matrix;

b) separating the solid phase matrix having immunoglobulins bound thereto from the solution;

c) optionally washing the solid phase matrix; and d) contacting the solid phase matrix with an eluent in order to liberate the one or more immunoglobulins from the solid phase matrix;

with the first proviso that at least two of the criteria (a), (b), and (c) are fulfilled:

(a) the solid phase matrix has a binding efficiency of at least 50% when tested at a pH in the range of 2.0 to 10.0 in the "*Standard Immunoglobulin Binding Test*" described herein; or (b) the solid phase matrix has an average binding efficiency of at least 60% for all of the immunoglobulins tested in the "*Monoclonal Antibody Array Binding Test*" when tested at a pH in the range of 2.0 to 10.0; or (c) the stability of the solid phase matrix in 1 M NaOH is so that incubation of the matrix in 1 M NaOH in the dark at room temperature for 7 days reduces the binding efficiency at a pH in the range of one pH unit lower than the binding maximum pH value to one pH unit higher than the binding maximum pH value, as determined in the "*Standard Immunoglobulin Binding Test*" described herein, with less than 25% compared to a corresponding untreated matrix; and with the second proviso that the molecular weight of the ligand -L is at the most 500 Dalton.

The present invention furthermore provides a solid phase matrix, comprising a functionalised matrix backbone carrying a plurality of functional groups of the following formula $$M\text{-}SP1\text{-}L$$

wherein M designates the matrix backbone, SP1 designates a spacer, and L designates a ligand comprising a mono- or bicyclic optionally substituted aromatic or heteroaromatic moiety, and wherein at least two of the criteria (a), (b), and (c) are fulfilled:

(a) the solid phase matrix has a binding efficiency of at least 50% when tested at a pH in the range of 2.0 to 10.0 in the "Standard Immunoglobulin Binding Test" described herein; or (b) the solid phase matrix has a binding efficiency of at least 40% for all of the immunoglobulins tested in the "Monoclonal Antibody Array Binding Test" when tested at a pH in the range of 2.0 to 10.0; or (c) the stability of the solid phase matrix in 1 M NaOH is so that incubation of the matrix in 1 M NaOH in the dark at room temperature for 7 days reduces the binding efficiency at a pH in the range of one pH unit lower than the binding maximum pH value to one pH unit higher than the binding maximum pH value, as determined in the "Standard Immunoglobulin Binding Test" described herein, with less than 25% compared to a corresponding untreated matrix;

with the first proviso that the molecular weight of the ligand -L is at the most 500 Dalton: and with the second proviso that when M is agarose and SP1 is derived from vinyl sulfone then L is not 4-aminobenzoic acid, which is especially suited for use in the method according to the invention.

It has furthermore been found that the matrices mentioned above, wherein the aromatic or heteroaromatic moiety is carrying an acidic group, optionally via a spacer SP2, are equally suited for the isolation and purification of proteins without the need to add lyotropic salts to the protein containing solution (the raw material) and without the need to use large amounts of organic solvents for elution of the bound proteins from the matrix.

Thus, the present invention also provides a solid phase matrix, comprising a functionalised matrix backbone carrying a plurality of functional groups of the following formula

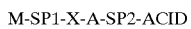

wherein M designates the matrix backbone; SP1 designates a spacer; X designates —O—, —S—, or —NH—; A designates a mono- or bicyclic optionally substituted aromatic or heteroaromatic moiety; SP2 designates an optional spacer; and ACID designates an acidic group;

with the first proviso that the molecular weight of the ligand -L is at the most 500 Dalton; and with the second proviso that when M is agarose and SP1 is derived from vinyl sulfone then L is not 4-aminobenzoic acid;

and a method for the isolation of proteins from a solution containing one or more of proteins, comprising the following operations:

a) contacting a solution containing one or more proteins having a pH in the range of 1.0 to 6.0 and a total salt content corresponding to an ionic strength of at the most 2.0 with a solid phase matrix as described herein, whereby at least a part of the proteins becomes bound to the solid phase matrix;

b) separating the solid phase matrix having proteins bound thereto from the solution;

c) optionally washing the solid phase matrix; and d) contacting the solid phase matrix with an eluent in order to liberate one or more of the proteins from the solid phase matrix, wherein the eluent used comprises less than 10% (v/v) of organic solvents.

DETAILED DESCRIPTION OF THE INVENTION

Isolation of Immunoglobulins

In general, the method for isolation of immunoglobulins may be divided into several steps:

(a) Equilibration of the solid phase matrix (b) Contacting the solid phase with immunoglobulin solution (c) Washing the solid phase (d) Separation of the solid phase from the solution (d) Elution of the bound immunoglobulin (e) Regeneration of the solid phase matrix It may however depend on the specific application whether all steps are performed each time or at all. Thus, the only mandatory steps are the contacting, separation, and the elution steps, while the equilibration, washing, and regeneration steps may or may not be performed according to the specific requirements relevant to the actual application. The type of the separation step depends on the actual set-up (see below).

Equilibration

Before contacting the solid phase matrix with the immunoglobulin containing solution it is preferred to ensured that both the matrix and the solution are in a condition resulting in the wanted binding of immunoglobulin. In this respect, it may therefore be necessary to adjust parameters such as pH, ionic strength, and temperature and in some instances the addition of substances of different kind to promote binding of immunoglobulins and/or to prevent binding of impurities.

Thus, it is an optional step to perform an equilibration of the solid phase matrix by washing it with a solution (e.g. a buffer for adjusting pH, ionic strength, etc., or for the introduction of a detergent) bringing the necessary characteristics to the solid phase.

Contacting

When the solid phase matrix is in the form of particles of either spherical or irregular form the contacting of a solution containing one or more immunoglobulins may be performed either in a packed bed column or in a fluidised/expanded bed column containing the solid phase matrix. It may also be performed in a simple batch operation where the solid phase matrix is mixed with the solution for a certain time to allow binding of the immunoglobulin(s).

Whenever the solid phase matrix is in the form of permeable or semi-permeable membranes or sheets the contacting is generally performed by pumping/forcing the immunoglobulin containing solution across the surface and/or through a porous structure of the membrane or sheet to ensure that the immunoglobulins are coming in close contact with the ligands immobilised on the surface and/or in the porous structures.

Further guidelines for this process are given in "Purification Tools for Monoclonal Antibodies", Gagnon, P., Validated Biosystems, 1996).

Washing

After contacting the solid phase matrix with the immunoglobulin containing solution there is optionally performed a washing procedure to remove unbound or loosely bound substances such as other proteins, lipids, nucleic acids or other impurities from the matrix. However in some cases where very high purity of the immunoglobulin is not critical the washing procedure may be omitted saving a process-step as well as washing solution.

In other cases where very high purity of the immunoglobulin is needed there may be employed several different washing procedures with different washing buffers before elution is commenced.

The washing buffers employed will depend on the nature of the chromatographic adsorbent and the ligand binding the immunoglobulins. The washing buffer should not disturb the binding of the immunoglobulin to the adsorbent i.e. pH, salt concentration and other additives should be adjusted so that only the unwanted impurities are removed either by simple substitution of the solution containing impurities and present in and around the adsorbent with the washing buffer—or in combination herewith also releasing impurities bound to the adsorbent. The releasing of impurities bound to the matrix may be accomplished either by changing pH and/or ionic strength or by adding a substance to the washing buffer which interacts competitively with either the adsorbent or the impurity, and thereby displacing the impurity from the adsorbent.

The washing (operation (c) in the method according to the invention) is preferably performed in order to remove remainders from the solution containing the immunoglobulins, and in order to remove other type of biomolecules.

Elution

Elution of the bound immunoglobulin is generally performed by contacting the solid phase matrix comprising the bound immunoglobulin with a solution that releases the immunoglobulin from the ligand on the matrix. The immunoglobulin is hereby released into the solution and can be washed out of the matrix. The solution employed to release the immunoglobulin should generally have different characteristics than what was used for binding of the immunoglobulin e.g. the solution may have a different pH, a different ionic strength, a different temperature and/or it may comprise organic solvents (preferably only small amounts), detergents, chaotropes or other denaturing reagents. Combinations of changes in these different parameters are also generally employed.

Elution may also be performed by applying a solution gradually changing the conditions from binding to non-binding conditions, a procedure which typically is phrased gradient elution.

Once the immunoglobulin have been released from the solid phase matrix into the eluting solution it may be recovered from this by different optional means known per se. In the most simple case the immunoglobulin may be used directly without any changes but in many instances some sort of concentrating procedure would be preferred e.g. ultra-filtration, freeze-drying or precipitation (e.g. salting out). The immunoglobulin solution may also very well be purified further in a further processing step of optional character.

Regeneration

The solid phase matrix may optionally by cleaned i.e. regenerated after elution of the immunoglobulin. This procedure is typically performed regularly to minimise the building up of impurities fouling up the surface of the solid phase and/or to sterilise the matrix to avoid contamination of the product with microorganisms proliferating and escaping from the solid phase and the equipment used during the process. Popular ways of performing such a regeneration step is to wash the solid phase matrix with solutions able to clean the matrix and/or kill microorganisms. Typical solutions for these purposes would be, e.g., 0.1–1.0 M sodium hydroxide; solutions of peracids or hydrogen peroxide; denaturants such as guanidinium hydrochloride; solutions comprising active chlorine such as hypochlorite solutions, organic solvents such as ethanol; detergents etc. An especially preferred method for this purpose is to use 0.1–1.0 M sodium hydroxide due to the very high efficiency, low cost, ease of neutralization with hydrochloric acid and lack of waste problems.

In a preferred embodiment of the present invention the method includes: (i) equilibration (optional step), (ii) contacting, (iii) washing (optional step), (iv) separation, (v) elution, and (vi) regeneration, where cycle of steps (i)–(v) are repeated one or several times before regeneration, and were the solid phase matrix is reused after regeneration.

The conditions employed in both the binding, washing and elution step(s) may be very decisive for the resulting binding efficiency, yield and purity of the immunoglobulin. Different solid phase matrices according to the invention may need different binding, washing and elution conditions to ensure an optimal result. Likewise the nature of the raw material will have a very significant impact on the conditions chosen for that particular isolation procedure e.g. very dilute solutions of monoclonal antibodies in hybridoma cell culture supernatants (typically 10–100 $\mu$g/ml) behave differently than the same type of antibodies present in more concentrated solutions such as ascites fluids (1–5 mg/ml) and immunoglobulins present in, e.g., whey (1–2 mg/ml) need other conditions than immunoglobulins from plasma/serum (5–20 mg/ml) etc.

Also the composition i.e. the contents of different types of impurities may vary significantly between different raw materials, e.g., egg yolk has a very different composition as compared to hybridoma cell culture supernatants.

As mentioned above it is generally possible to add different substances to the immunoglobulin containing solution as to enhance the binding of antibodies to the solid phase matrix.

In a particular embodiment, the present invention relates to methods for the isolation of immunoglobulins and solid phase matrices therefor yielding an isolated immunoglobulin of a purity of at least 10% such as at least 30%, preferably at least 60% such as at least 70%, more preferably at least 80% such as 90%, in particular at least 99%.

As mentioned above, it is believed that the binding efficiency maximum pH value for the solid phase matrices is in the range of 2.0 to 10.0, most likely in the range of 3.0 to 9.0. It is therefore most relevant to conduct the isolation process near that maximum (which of course may vary for different combinations of immunoglobulins/solid phase matices. Thus, the pH of the solution containing the immunoglobulins (or proteins in general) is preferably in the range of 2.0 to 10, such as in the range of 3.0 to 9.0. However, depending on the ligand type and the matrix backbone, the pH range is preferably 3.0 to 7.0 or 6.0 to 9.0.

It is believed that, when the ligand is of the type -X-A-SP2-ACID, then should the pH of the solution containing the immunoglobulins be in the range of 2.0 to 6.0, preferably in the range of 2.5 to 5.5 such as in the range of 3.0 to 5.5, or in the range of 4.0 to 5.5, corresponding to an expected binding efficiency maximum for that specific type of matrix.

With respect to contacting operation (a) above, it has been found that it is not necessary to add excessive amounts of lyotropic salt in order for the immunoglobulins to bind to the matrix. Thus, the total salt content, including e.g. NaCl, of the solution containing the immunoglobulins need only be so that it corresponds to a ionic strength of at the most 2.0, preferably in the range of 0.05 to 2.0, such as 0.05 to 1.4, especially in the range of 0.05 to 1.0. As an alternative requirement, the concentration of lyotropic salt as such should be as low as possible, thus, it has been shown that it is possible to operate with a solution containing immunoglobulins where the concentration of lyotropic salts is at the most 0.4 M, preferably at the most 0.3 M, in particular at the most 0.2 M, such as at the most 0.1 M.

Examples of lyotropic salts are given in "Purification Tools for Monoclonal Antibodies", Gagnon, P., Validated Biosystems, 1996), where the Hofmeister series of lyotropic ions are presented.

With respect to the concentration of immunoglobulins in the solution, it is believed that the solid phase matrices can operate for a very large range concentration range, thus, it is believed that the solid phase matrices operate equally efficient for concentration of immunoglobulins in the solution containing the immunoglobulins in the range of 0.001 to 0.2, preferably 0.01 to 0.1, mg/ml, as in hybridoma cell culture supernatants, in the range of 0.2 to 2.0 mg/ml as in milk and whey, in the range of 5.0 to 20 mg/ml as for different animal sear and plasma, and even in the range of 20–80 mg/ml as for colostrum.

It has been found that the present invention is especially suitable for solutions comprising in the range of 0.1 to 30 mg immunoglobulins per gram of solid phase matrix, such as in the range of 0.2 to 2 or in the range of 5.0 to 25 mg per gram of solid phase matrix.

Thus, the solution containing the immunoglobulins may be artificially as well as biologically solution of immunoglobulins such as crude fermentation broths; mammalian cell cultures such as hybridoma cell cultures; fermentation broths from cultures of genetically engineered microorganisms such as *E.coli*; ascites fluids such as mouse and rat ascites fluid; milk, whey, blood, plasma and serum from man, mouse, rat, cow, pig, rabbit, goat, guinea pig, and donkey; and egg yolk such as chicken egg yolk.

Furthermore, it has been shown (see the examples) that special advantages with respect to purity may be obtained when the solution containing the immunoglobulins comprises a negatively charged detergent. Without being bound to any theory it is believed that the detergent suppresses the adherence of other biomolecules to the matrix. Examples of such detergent are octyl sulfate, bromphenol blue, octane sulfonate, sodium laurylsarcosinate, and hexane sulfonate.

Also, in the washing step (operation (c) of the method according to the invention) it is, probably for the same reasons, advantageous to use an negatively charged detergent. The detergent may be used alone or in combination with an buffer, e.g. a lyotropic salt buffer. Use of lyotropic salts in the washing step (small volume) represents only a minor waste product problem compared with using lyotropic salts in the binding processes (operation (a)) (in that the binding process includes the use of large volumes is most cases).

Also, the excellent properties of the solid phase matrices for use in the method according to the invention may be expressed even without the use of organic solvents in the elution step (operation (d)), thus, preferably, the eluent used comprises less than 10% (v/v), more preferably less than 5%, of organic solvents. Most preferably, no organic solvents are used at all.

Alternatively, as has been shown in example 14, a larger amount of non-toxic solvents, e.g. propylene glycol, may be used, e.g. up to 40% propylene glycol.

The contacting step (operation (a)) as well as the following step, i.e. separation, washing, and eluation, may be performed in various way. The physical measures selected are often guided by the scale and whether the process has to be repeated. The solid phase matrices according to the invention may be used in almost any of the set-ups used for development and for industrial purposes. Thus, the solid phase matrix may be contacted with the solution containing the immunoglobulins, e.g., in a stirred batch process, in a packed bed chromatographic column process, and in a fluidised bed process. Further guidelines are given in "Purification Tools for Monoclonal Antibodies", Gagnon, P., Validated Biosystems, 1996).

Other necessary measures for performing the isolation of immunoglobulins according to the invention follow conventional methodologies.

The present invention provides a method for the isolation and purification of immunoglobulins from a large variety of raw materials having different concentrations of immunoglobulins, typically ranging from about 10 µg/ml in hybridoma cell culture supernatants and about 1–2 mg/ml in milk and whey to about 5–20 mg/ml in different animal sera/plasma, and up to 50–60 mg/ml in colostrum. The nature and relative concentration of different impurities potentially interfering with the binding and isolation of immunoglobulins are also varying to a great extent between the different immunoglobulin sources.

For some applications of immunoglobulins it is of high important that the immunoglobulins are extremely pure, e.g. having a purity of more than 99%. This is particularly true whenever the immunoglobulin is to be used as a therapeutic, but is also necessary for other applications. In the diagnostic field the degree of purity needed may depend on a number of factors such as whether the antibody is to be used un-derivatised, in which case there may not be required a high degree of purity, i.e. less than 50%, or whether the antibody has to be labelled with a signal molecule such as an enzyme, e.g. horseradish peroxidase, in which case the antibody often is required to be at least 80% pure or more. For other applications the need for purity may differ correspondingly. It seems however to be a general demand that the purity of the immunoglobulin is at least 10% on a dry matter basis to enable a proper use of the product. However, the present invention provides, as it should be clear, guidelines for solving these problems.

Solid Phase Matrices

As described above, the method according to the invention includes the use of a solid phase matrix, where the solid phase matrix comprises a functionalised matrix backbone carrying a plurality of functional groups of the following formula

M-SP1-L wherein M designates the matrix backbone, SP1 designates a spacer, and L designates a ligand comprising an mono- or bicyclic optionally substituted aromatic or heteroaromatic moiety, which has to fulfil certain criteria.

It should be noted that the present invention also relates to these solid phase matrices as such. Thus, the definitions below relate to the method according to the invention as well as to the solid phase matrices according to the invention.

The solid phase matrix may comprise, as the matrix backbone, any natural or synthetic and organic or inorganic material known per se to be applicable in solid phase separation of proteins and other biomolecules, e.g. natural or synthetic polysaccharides such as agar-agar and agaroses; celluloses, cellulose ethers such as hydroxypropyl cellulose, carboxymethyl celluose; starches; gums such as guar gum, and gum arabic, gum ghatti, gum tragacanth, locust bean gum, xanthan gum; pectins; mucins; dextrans; chitins; chitosans; alginates; carrageenans; heparins; gelatins; synthetic polymers such as polyamides such as polyacrylamides and polymethacrylamides; polyimides; polyesters; polyethers; polymeric vinyl compounds such as polyvinylalcohols and polystyrenes; polyalkenes; inorganic materials such as silicious materials such as silicon dioxide including amorphous silica and quartz; silicas; metal silicates, controlled pore glasses and ceramics; metal oxides and sulfides, or combinations of these natural or synthetic and organic or inorganic materials.

The matrix backbone is preferably selected from agar-agar, agaroses, celluloses, cellulose ethers such as hydroxypropyl cellulose, carboxymethyl cellulose, polyamides such as poly(meth)acryl-amides, polyvinylalcohols, silicas, and controlled pore glasses.

Especially interesting solid phase materials as matrix backbones are e.g. agar or agarose beads such as Sepharose and Superose beads from Pharmacia Biotech, Sweden and Biogel A from Biorad, USA; dextran based beads such as Sephadex, Pharmacia Biotech; cellulose based beads and membranes such as Perloza cellulose from Secheza, Czechoslovakia; composite beads such as Sephacryl and Superdex, Pharmacia Biotech; beads of synthetic organic polymers such as Fractogel from Toso-Haas, USA; POROS media from Perceptive Biosystems, USA, Bio-Rex, Bio-Gel P and Macro Prep from Biorad, HEMA and Separon from TESSEK and Hyper D and Trisacryl media from BioSepra, USA, Enzacryl and Azlactone, 3M, USA; beads of siliceous materials such as controlled pore glass, PROSEP, from Bioprocesing, England and Spherocil, BioSepra; and coated silica composites in the form of beads or membranes such as ACTI-DISK, ACTI-MOD and CycloSep from Arbor Technologies, USA.

Typically, the solid phase matrix backbone, as well as the resulting functionalised solid phase matrix, may, e.g., be in the form of irregular particles or spherical beads, membranes or sheets, moulded surfaces, or sticks. The solid phase material may further be fully or partly permeable or completely impermeable to proteins. In a particularly interesting embodiment of the present invention, the matrix is in the form of irregular or spherical beads with sizes in the range of 1–10000 $\mu$m, preferably 10–1000 $\mu$m; such as 10–60 $\mu$m for high performance applications and such as 50–500 $\mu$m, preferably 50–300 $\mu$m, for preparative purposes.

A particular interesting form of matrix is a density controlled matrix in the form of a conglomerate comprising density controlling particles. These conglomerates, which are especially applicable in large scale operations for fluidised or expanded bed chromatography as well as different batch-wise chromatography techniques in non-packed columns, e.g. simple batch adsorption in stirred tanks, are described in the WO 92/00799, which is hereby incorporated by reference.

The ligands L may be attached to the solid phase material by any type of covalent bond known per se to be applicable for this purpose, either by a direct chemical reaction between the ligand and the solid phase material or by a preceding activation of the solid phase material or of the ligand with a suitable reagent known per se making it possible to link the matrix backbone and the ligand. Examples of such suitable activating reagents are epichlorohydrin, epibromohydrin, allyl-glycidylether; bis-epoxides such as butanedioldiglycidylether; halogen-substituted aliphatic compounds such as di-chloro-propanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allyl-glycidylether; bis-epoxides; halogen-substituted aliphatic compounds; divinyl sulfone; aldehydes; quinones; cyanogen bromide; chloro-triazines; oxazolones; maleimides; pyridyl disulfides; and hydrazides, are preferred.

Especially interesting activating reagents are believed to be epoxy-compounds such as epichlorohydrin, allyl-glycidylether and butanedioldiglycidylether.

In certain instances the activating reagent may even constitute a part of the functionality contributing to the binding of immunoglobulins to the solid phase matrix, e.g. in cases where divinyl sulfone is used as the activating reagent. In other cases the activating reagent is released from the matrix during reaction of the functional group with the matrix. This is the case when carbodiimidazoles and carbodiimides are used.

The above mentioned possibilities makes it relevant to define the presence of an optional spacer SP1 linking the matrix M and the ligand L. In the present context the spacer SP1 is to be considered as the part of the activating reagent which forms the link between the matrix and the ligand. Thus, the spacer SP1 corresponds to the activating reagents and the coupling reactions involved. In some cases, e.g. when using carbodiimides, the activating reagent forms an activated form of the matrix or of the ligand reagent. After coupling no parts of the activating reagent is left between the ligand and the matrix, and, thus, SP1 is simply a single bond.

In other eases the spacer SP1 is an integral part of the functional group effecting the binding characteristics, i.e. the ligand, and this will be especially significant if the spacer SP1 comprises functionally active sites or substituents such as thiols, amines, acidic groups, sulfone groups, nitro groups, hydroxy groups, nitrile groups or other groups able to interact through hydrogen bonding, electrostatic bonding or repulsion, charge transfer or the like.

In still other cases the spacer SP1 may comprise an aromatic or heteroaromatic ring which plays a significant role for the binding characteristics of the solid phase matrix. This would for example be the case if quinones or chloro-triazines where used as activation agents for the solid phase matrix or the ligand.

Preferably, the spacer SP1 is a single bond or a biradical derived from an activating reagent selected from epichlorohydrin, allyl-glycidylether, bis-epoxides such as butanedioldiglycidylether, halogen-substituted aliphatic compounds such as 1,3-dichloropropan-2-ol, aldehydes such as glutaric dialdehyde, divinyl sulfone, quinones, cyanogen bromide, chloro-triazines such as cyanuric chloride, 2-fluoro-1-methylpyridinium toluene-4-sulfonates, maleimides, oxazolones, and hydrazides.

Preferably the spacer SP1 is selected from short chain aliphatic biradicals, e.g. of the formula —$CH_2$—$CH(OH)$—$CH_2$—(derived from epichlorohydrin), —$(CH_2)_3$—O—$CH_2$—$CH(OH)$—$CH_2$— (derived from allyl-glycidylether) or —$CH_2$—$CH(OH)$—$CH_2$—O—$(CH_2)_4$—O—$CH_2$—$CH(OH)$—$CH_2$— (derived from butane-dioldiglycidylether; or a single bond.

Due to the risk of leakage of material (e.g. the ligand and/or the spacer) from a solid phase matrix into the eluted product (e.g. the immunoglobulin) the molecular weight of the ligand (or the ligand+the optional spacer) is advantageously chosen as low as possible. A major drawback of using protein A, protein G, synthetic peptides and other relatively high molecular weight ligands (e.g. dyes) is that it may be difficult or even impossible to separate any released ligand (optionally including the spacer) from the eluted immunoglobulin due to the small difference between the respective molecular weights and the natural tendency of the components to bind to each other. This may have a detrimental effect in those cases where the immunoglobulin is to be used as a therapeutic agent causing allergic chock or other serious symptoms in the patient. The smaller the molecular weight of the ligand (including its spacer) the more efficient can any leaked ligand be separated from the immunoglobulin product. Another significant advantage of having the smallest possible molecular weight of the ligand (or the ligand-spacer arm conjugate) is that any leaked material, which may not have been separated from the immunoglobulin prior to injection/ingestion in the patient will elucidate a minimum of antigenicity the lower the molecular weight and therefore in general be relatively more acceptable to the organism than higher molecular weight ligands.

It is therefore, preferred that the ligand L has a molecular weight below 500 Dalton, preferably below 400 Dalton, more preferably below 300 Dalton, such as below 250 Dalton, or even below 200 Dalton.

With respect to the ligand-spacer arm conjugate (-SP1-L), it is preferred that the molecular weight is below 500 Dalton, more preferably below 400 Dalton, such as below 300 Dalton, or even below 260 Dalton.

According to the invention, the matrix comprises ligands which either alone or in combination with a spacer SP1 (and even the matrix backbone) make it possible to bind immunoglobulins thereto. It is found that a crucial part of the ligand is a mono- or bicyclic aromatic or heteroaromatic moiety which may carry one or more substituents, one of which preferably being a substituent comprising an acidic moiety.

The term "mono- or bicyclic" is intended to mean that the core part of the moiety in question is consisting of one ring or two fused rings, e.g. as in benzene and naphthalene, respectively, and, thus, not to ligands comprising two separate rings as in biphenyl.

It has been found that the structure of the aromatic or heteroaromatic part of the ligand, L, may cover a very wide spectrum of different structures optionally having one or more substituents on the aromatic or heteroaromatic ring(s). However, it seems to be rather decisive which substituents are present on, e.g., a benzene ring as to whether the ligand will bind the immunoglobulin(s) efficiently, which is the object of the present invention, or whether the binding is only moderately or low.

Even though the ligands are named here and in the following using the nomenclature corresponding to the individual and discrete chemical compound, from which they are derived, it should be understood that the actual ligand L is a radical of such a compound.

However, based on our preliminary findings, it is especially preferred to employ matrices comprising aromatic or heteroaromatic groups (radicals) of the following types as functional groups: benzoic acids such as 2-aminobenzoic acids, 3-aminobenzoic acids, 4-aminobenzoic acids, 2-mercaptobenzoic acids, 4-amino-2-clorobenzoic acid, 2-amino-5-chlorobenzoic acid, 2-amino-4-chlorobenzoic acid, 4-aminosalicylic acids, 5-aminosalicylic acids, 3,4-diaminobenzoic acids, 3,5-diaminobenzoic acid, 5-aminoisophthalic acid, 4-aminophthalic acid; cinnamic acids such as hydroxy-cinnamic acids; nicotinic acids such as 2-mercaptonicotinic acids; naphthoic acids such as 2-hydroxy-1-naphthoic acid; quinolines such as 2-mercaptoquinoline; tetrazolacetic acids such as 5-mercapto-1-tetrazolacetic acid; thiadiazols such as 2-mercapto-5-methyl-1,3,4-thiadiazol; benzimidazols such as 2-amino-benzimidazol, 2-mercaptobenzimidazol, and 2-mercapto-5-nitro-benzimidazol; benzothiazols such as 2-aminobenzothiazol, 2-amino-6-nitrobenzothiazol, 2-mercaptobenzothiazol and 2-mercapto-6-ethoxybenzothiazol; benzoxazols such as 2-mercaptobenzoxazol; thiophenols such as thiophenol and 2-aminothiophenol; 2-(4-aminophenylthio)acetic acid; aromatic or heteroaromatic sulfonic acids and phosphonic acids, such as 1-amino-2-naphthol-4-sulfonic acid and phenols such as 2-amino-4-nitrophenol. It should be noted that the case where M is agarose, SP1 is derived from vinyl sulfone, and L is 4-amino-benzoic acid is specifically disclaimed in relation to the solid phase matrices according to the invention of WO 92/16292.

The detailed structure of the ligand seems to determine important functional characteristics relevant for the isolation of immunoglobulins from different sources. Thus, different ligands comprising remote or closely related aromatic structures seems to result in significant changes in the binding strength, binding selectivity, binding capacity and overall yield of immunoglobulin when applied in the isolation of antibodies from different raw materials.

For binding of immunoglobulins at near neutral pH (about pH 5 to pH 9) it is preferred to use a ligand comprising radicals derived from a benzene ring fused with a heteroaromatic ring system, e.g. a ligand selected from benzimidazoles such as 2-mercapto-benzimidazol and 2-mercapto-5-nitro-benzimidazol; benzothiazols such as 2-amino-6-nitrobenzothiazol, 2-mercaptobenzothiazol and 2-mercapto-6-ethoxybenzothiazol; benzoxazols such as 2-mercaptobenzoxazol. Not belonging to the former group of ligands but also preferred for the binding of immunoglobulins at near neutral pH are ligands chosen from the group of thiophenols such as thiophenol and 2-aminothiophenol.

Thus, as it is clear from the above and the results shown herein, the ligand L is preferably selected from radicals having the following formula

-X-A-SUB wherein X designates —O—, —S—, or —NH—, A designates an aromatic or heteroaromatic ring or ring system, and SUB designates one or more substituents.

It is understood that X is an integral part of the ligand in that the aromatic or heteroaromatic compound which forms the ligand part of the solid phase matrix after reaction with an activated matrix backbone, must include a hydroxygroup (X is —O—), a mercapto group (X is —S—) or an amino group (X is —NH—) directly attached the aromatic or heteroaromatic moiety. Examples of such compounds are 3-hydroxy-cinnamic acid, 2-mercapto-benzoic acid, and 2-amino-benzoic acid. It should be understood that if the aromatic or heteroaromatic compound comprises, e.g., a hydroxy group as well as an amino group, the resulting solid phase matrix may comprise a mixture of ligand being attached to the linker through the amino group and through the hydroxy group, respectively.

The aromatic radicals are preferably selected from benzene radicals and naphthalene radicals.

The aromatic radical is preferably a benzene radical such as phenyl, 1,2-phenylene, 1,3-phenylene, 1,4-phenylene, 1,2,3-benzenetriyl, 1,2,4-benzenetriyl, 1,3,5-benzenetriyl, 1,2,3,4-benzenctetrayl, 1,2,3,5-benzenetetrayl, 1,2,4,5-benzenetetrayl, and 1,2,3,4,5-benzenepentayl.

The heteroaromatic radicals are preferably selected from monocyclic heteroaromatic radicals such as thiophene, furan, pyran, pyrrole, imidazole, pyrazole, isothiazole, isoxazole, pyridine, pyrazine, pyrinidine, and pyridazine radicals; and bicyclic heteroaromatic radicals such as indole, purine, quinoline, benzofuran, benzimidazole, benzothiazole, and benzoxazole radicals.

The heteroaromatic radical is preferably selected from radicals of pyridine, benzimidazole, benzothiazole and benzoxazole.

A preferred group of ligands for high purity immunoglobulin isolates is chosen among amino-benzoic acids like 2-amino-benzoic acid, 2-mercapto-benzoic acid, 3-aminobenzoic acid, 4-amino-benzoic acid, 4-amino-2-chlorobenzoic acid, 2-amino-5-chlorobenzoic acid, 2-amino-4-chlorobenzoic acid, 4-aminosalicylic acids, 5-aminosalicylic acids, 3,4-diaminobenzoic acids, 3,5-diaminobenzoic acid, 5-aminoisophthalic acid, 4-aminophthalic acid.

Another preferred group of ligands giving a high degree of purity of the isolated immunoglobulin is the group of cinnamic acids such as 2-hydroxy-cinnamic acids, 3-hydroxy-cinnamic acid and 4-hydroxy-cinnamic acid.

Still another preferred group of ligands for isolation of high purity immunoglobulins are derived from the group of heteroaromatic compounds comprising a carboxylic acid and an amino group as substituents such as 2-amino-nicotinic acid, 2-mercapto-nicotinic acid, 6-amino-nicotinic acid and 2-amino-4-hydroxypyrimidine-carboxylic acid.

Agarose matrix backbones and spacers derived from epoxy compounds are especially relevant in combination with these preferred groups of ligands.

With respect to the substituents on the aromatic or heteroaromatic moiety, SUB preferably comprises at least one acidic group.

In a particularly interesting embodiment of the present invention, SUB comprises at least one substituent of the following formula

-SP2-ACID wherein SP2 designate an optional second spacer and ACID designates an acidic group.

In the present context the term "acidic group" is intended to mean groups having a pKa-value of less than about 6.0, such as a carboxylic acid group (—COOH), sulfonic acid group (—SO$_2$OH), sulfinic acid group (—S(O)OH), phosphinic acid group (—PH(O)(OH)), phosphonic acid monoester groups (—P(O)(OH)(OR)), and phosphonic acids group (—P(O)(OH)$_2$). The pKa-value of the acidic group should preferably be in the range of 1.0 to 6.0.

The acidic group is preferably selected from carboxylic acid, sulfonic acid, and phosphonic acid.

The group SP2 is selected from $C_{1-6}$-alkylene, and $C_{2-6}$-alkenylene, or SP2 designates a single bond. Examples of relevant biradicals are methylene, ethylene, propylene, propenylene, iso-propylene, and cyclohexylene. Preferably, SP2 designates methylene, ethylene, or a single bond.

In one embodiment of the present invention SUB designates one group -SP2-ACID. In this case, SP2 is preferably a single bond.

SUB may, however, designate a substituent -SP2-ACID as well as one or more further substituent(s) independently selected from hydroxy, amino, cyano, mono- and di($C_{1-6}$-alkyl)amino, halogen such as iodo, bromo, chloro, and fluoro, sulfanyl, nitro, $C_{1-6}$-alkylcarboxy, and aminocarboxy, mono- and di($C_{1-6}$-alkyl)aminocarboxy, carboxy, sulfono, sulfonamide, phosphonic ester with $C_{1-6}$-alkyl, optionally substituted $C_{1-12}$-alkyl, optionally substituted $C_{2-12}$-alkenyl, optionally substituted $C_{1-12}$-alkynyl, and optionally substituted $C_{1-12}$-alkoxy, thioester, or the substituent is an oxygen atom which together with two valences of a carbon atom of the aromatic or heteroaromatic moiety form an oxo group. Furthermore, SUB may designate a further group -SP2-ACID as defined above. It should be understood that the substituents defined for SUB correspond to the optional substituents for L.

In another preferred embodiment, SUB designates a substituent -SP2-ACID as well as one or more further substituent(s) independently selected from hydroxy, amino, cyano, halogen, sulfanyl, nitro, optionally substituted $_{1-6}$-alkyl methyl, ethyl, propyl, butyl, isobutyl, and cyclohexyl, optionally substituted $C_{2-6}$-alkenyl, optionally substituted $C_{2-6}$-alkynyl, optionally substituted $C_{1-6}$-alkoxy, carboxy, and sulfono, or the substituent is an oxygen atom which together with two valences of a carbon atom of the aromatic or heteroaromatic moiety form an oxo group. Also in this case, SP2 preferably designates methylene, ethenylene, or a single bond, preferably a single bond.

In the present context, the term "$C_{1-12}$-alkyl" is intended to mean alkyl groups with 1–12 carbon atoms which may be straight or branched or cyclic such as methyl, ethyl, propyl, isopropyl, butyl, isobutyl, tert-butyl, pentyl, hexyl, octyl, dodecyl, cyclopentyl, cyclohexyl, decalinyl, etc.

The term "optionally substituted $C_{1-12}$-alkyl" is intended to mean a $C_{1-12}$-alkyl group which may, be substituted with one or more, preferably 1–3, groups selected from carboxy; protected carboxy such as a carboxy ester, e.g. $C_{1-6}$-alkoxycarbonyl; aminocarbonyl; mono- and di($C_{1-6}$-alkyl)-aminocarbonyl; amino-$C_{1-6}$-alkyl-aminocarbonyl; mono- and di($C_{1-6}$-alkyl)amino-$C_{1-6}$-alkyl-aminocarbonyl; amino; mono- and di($C_{1-6}$-alkyl)amino; $C_{1-6}$-aklylcarbonylamino; hydroxy; protected hydroxy such as acyloxy, e.g. $C_{1-6}$-alkanoyloxy; sulfono; $C_{1-6}$-alkylsulfonyloxy; nitro; phenyl; phenyl-$C_{1-6}$-alkyl; halogen; nitrilo; and mercapto.

Examples of substituted $C_{1-12}$-alkyl groups are carboxy-$C_{1-12}$-alkyl (e.g. carboxymethyl and carboxyethyl), protected carboxy-$C_{1-12}$-alkyl such as esterified carboxy-$C_{1-6}$-alkyl (e.g. $C_{1-6}$-alkoxy-carbonyl-$C_{1-12}$-alkyl such as methoxycarbonylmethyl, ethoxycarbonylmethyl, and methoxycarbonylethyl), aminocarbonyl-$C_{1-12}$-alkyl (e.g. aminocarbonylethyl, aminocarbonylethyl and aminocarbonylpropyl), $C_{1-6}$-alkylaminocarbonyl-$C_{1-12}$-alkyl (e.g. methylaminocarbonymethyl and ethylaminocarbonylmethyl), amino-$C_{1-6}$-alkyl-aminocarbonyl-$C_{1-12}$-alkyl (e.g. aminomethylaminocarbonylmethyl and aminoethylaminocarbonylmethyl), mono- or di($C_{1-6}$-alkyl)amino-$C_{1-6}$-alkylaminocarbonyl-$C_{1-12}$-alkyl (e.g. dimethylaminomethylaminocarbonylmethyl and dimethylaminoethylaminocarbonylmethyl), mono- or di($C_{1-6}$-alkyl)amino-$C_{1-12}$-alkyl (e.g. di-methylaminomethyl and dimethylaminoethyl), hydroxy-$C_{1-12}$-alkyl (e.g. hydroxymethyl and hydroxyethyl), protected hydroxy-$C_{1-12}$-alkyl such as acyloxy-$C_{1-12}$-alkyl (e.g. $C_{1-6}$-alkanoyloxy-$C_{1-12}$-alkyl such as acetyloxyethyl, acetyloxypropyl, acetyloxybutyl, acetyloxypentyl, propionyloxy-methyl, butyryloxymethyl, and hexanoyloxymethyl).

In the present context, the term "$C_{2-12}$-alkenyl" is intended to mean mono-, di- or polyunsaturated alkyl groups with 2–12 carbon atoms which may be straight or branched or cyclic in which the double bond(s) may be present anywhere in the chain or the ring(s), for example vinyl, 1-propenyl, 2-propenyl, hexenyl, decenyl, 1,3-heptadienyl, cyclohexeyl etc. Some of the substituents exist both in a cis and a trans configuration. The scope of this invention comprises both the cis and trans forms.

In the present context, the term "$C_{2-12}$-alkynyl" is intended to mean a straight or branched alkyl group with 2–12 carbon atoms and incorporating one or more triple bond(s), e.g. ethynyl, 1-propynyl, 2-propynyl, 2-butynyl, 1,6-heptadiynyl, etc.

In the expressions "optionally substituted $C_{2-12}$-alkenyl" and "optionally substituted $C_{2-12}$-alkynyl", the term "optionally substituted" is intended to mean that the moiety may be substituted one or more times, preferably 1–3 times, with one of the groups defined above for "optionally substituted $C_{1-12}$-alkyl".

The term "optionally substituted $C_{1-12}$-alkoxy", designates, as in traditional chemical nomenclature, an optionally substituted $C_{1-12}$-alkyl-oxy group, which may be substituted one or more times, preferably 1–3 times, with the substituents indicated for "optionally substituted alkyl" described above.

The terms "$C_{1-6}$-alkyl", "$C_{2-6}$-alkenyl", "$C_{2-6}$-alkynyl", and "$C_{1-6}$-alkoxy" reflect the shorter analogues of the "$C_{1-12}$-alkyl", "$C_{2-12}$-alkenyl", "$C_{2-12}$-alkynyl" and "$C_{1-12}$-alkoxy" groups.

The terms "$C_{1-6}$-alkylene" and "$C_{2-6}$-alkenylene" is intended to mean biradicals of the groups defined for "$C_{1-6}$-alkyl" and "$C_{2-6}$-alkenyl", respectively.

The present invention should not be bound to any specific theory, however, it is envisaged that the special electronic configuration of the aromatic or heteroaromatic moiety in combination with one or more heteroatoms, which may be located in the heteroaromatic ring system or as a substituent thereon, is involved in the specific binding of immunoglobulins, as well as the binding of other proteins.

Thus, in an interesting embodiment of the present invention the ligand comprises at least one nitrogen, sulfur or phosphorous atom, e.g. as a ring atom or as a substituent on the hetero)aromatic ring, such as an amino or nitro group or a sulfonic acid group or a phosphonic acid group.

An especially interesting combination of substituents seem to be any combination of at least one amino or mercapto group with at least one acidic group selected from carboxylic acids, sulfonic acids, and phosphonic acids.

It is envisaged that a combination of two or more of the ligands type defined herein on the same matrix backbone may lead to certain to certain advantages with respect to high binding efficiency and/or high purity of the immunoglobulin. However, in an important embodiment of the present invention, all of the functional groups on the solid phase matrix are substantially identical.

It may also be found to enhance binding efficiency and purity of the product by coupling the ligand to a matrix already comprising negatively or positively charged moieties such as positively charged amino-groups or negatively charged carboxylic acid, sulfonic acid or phosphonic acid groups.

The ligand concentration may also be of major significance for the functional characteristics of a matrix according to the invention e.g. a ligand may show a high degree of selective binding of immunoglobulins at one ligand concentration, while an increase in the ligand concentration results in a decrease in the binding selectivity. As is well-known to a person skilled in the art too high ligand concentrations may lead to strong binding of unwanted impurities by mechanism of multiple binding points, because the ligands are too closely spaced on the solid phase backbone. If the ligand concentration is kept low the ligands will be spaced with larger distances and therefore not course the binding of impurities by binding at multiple sites. Another negative effect of too high ligand concentration is the risk of binding the wanted protein e.g. the immunoglobulin by multiple binding sites. Such a multiple binding may lead to difficulties in releasing the protein e.g. the immunoglobulin with an appropriate elution buffer. In some instances it may even be necessary to utilise strongly denaturing conditions and/or organic solvents for release of the product from such to highly substituted solid phase matrices—with loss of biological activity as a consequence.

Ligand concentration of solid phase matrices may be disclosed in several different ways. One way of describing the ligand concentration is to disclose the amount of ligand present per gram of dry matter (e.g. in $\mu$mol/g dry matter). This is the result obtained directly if for example the ligand concentration is measured by elemental analysis of dried (e.g. freeze-dried) samples of the solid phase matrix. The ligand concentration may, however, also be disclosed as the amount of ligand present on one ml wet and sedimented solid phase matrix (also often referred to as one ml packed bed matrix). This is a figure which is easily calculated from a determination based on dried solid phase matrix (e.g. $\mu$mol/g dry matter), if the dry matter content of the hydrated solid phase matrix has been determined at the same time (i.e. gram of dry matter/ml wet sedimented solid phase matrix). Still another way of disclosing the ligand concentration is as the amount of ligand present in one gram of wet, but suction drained matrix. This figure is again easily calculated from a determination based on dry matter, if the solid phase dry matter content per gram of wet, but suction drained matrix has been determined at the same time.

Thus, the ligand concentration of the solid phase matrices of the invention is preferably in the range of 10–990 $\mu$mol/g dry matter of solid phase matrix, such as 100–990 $\mu$mol/g, more preferably 200–980 $\mu$mol/g, in particular 250–975 $\mu$mol/g; or the ligand concentration the solid phase matrices of the invention is preferably in the range of 1–145 $\mu$mol/ml of hydrated, sedimented solid phase matrix, such as 10–120 $\mu$mol/ml, more preferably 15–100 $\mu$mol/ml, in particular 20–80 $\mu$mol/ml; or the ligand concentration the solid phase matrices of the invention is preferably in the range of 1–130 $\mu$mol/g wet, but suction drained solid phase matrix, such as 10–110 $\mu$mol/gram, more preferably 20–100 $\mu$mol/g, in particular 20–90 $\mu$mol/gram.

It is, as should already be clear from the above, the aim of the present invention to provide solid phase matrices having a high binding efficiency.

Thus, the solid phase matrices, which are useful within the scope of the present invention must fulfil two of three criteria (a), (b), and (c) (see above), e.g. criteria (a) and (b), criteria (a) and (c), or criteria (b) and (c). Preferably all three criteria are fulfilled.

With respect to criterion (a), it is highly desirably in combination with the other criteria set forth herein or as an alternative thereto, that the solid phase matrix has a binding efficiency of at least 50% when tested at a pH in the range of 2.0 to 10.0 in the "*Standard Immunoglobulin Binding Test*" described herein. It is envisaged that the binding efficiency maximum (which can be estimated quite accurately, within half a pH unit, by testing the binding efficiency over an pH range using, e.g., increments of 0.5 pH units) of most of the matrices according to the invention is in the range of 3.0 to 9.0, e.g. in the range 3.0 to 7.0 or in the range of 6.0 to 9.0 depending on the nature of the ligand.

It has been found that the binding efficiency at pH 4.5 and pH 7.0 is especially relevant when performing a general evaluation of a solid phase matrix for isolation of immunoglobulins, thus, in a preferred embodiment, the present invention relates to a solid phase matrix having a binding efficiency of at least 50% at pH 4.5 or pH 7.0, in the "*Standard Immunoglobulin Binding Test*" described herein.

Thus, in a particularly interesting embodiment of the present invention, the solid phase matrix has a binding efficiency of at least 50%, preferably at least 60%, more preferably at least 70%, in particular at least 80%, such as at least 90%, in the "*Standard Immunoglobulin Binding Test*" described herein, at least one pH-value of the solvent in the range of pH 1.0 to pH 11.0, in particular in the range of pH 3.0 to pH 9.0, and more particularly at pH 4.5 or 7.0.

Furthermore, it is also the aim of the present invention to provide solid phase matrices which are able to bind a vide range of immunoglobulins, so that the end user can rely on one solid phase matrix instead of an number of products which has to be tested individually for each clone of immunoglobulins.

Thus, with respect to the criterion (b), the solid phase matrix preferably has an average binding efficiency of at least 50%, such as at least 60%, preferably at least 70%, especially at least 80%, in particular at least 90%, for the immunoglobulins tested in the "*Monoclonal Antibody Array Binding Test*" when tested at a pH in the range of 2.0 to 10.0, such as in the range of 3.0 to 9.0, e.g. in the range of 3.0 to 7.0 or in the range of 6.0 to 9.0. Typically, the binding efficiency is determined at two pH values, e.g. at pH 4.5 and pH 7.0, and the optimum is then found by varying the pH value in increments of 0.5 around the one of the two pH values giving the most promising binding efficiency.

The functional stability of the matrix, which is interesting and important with respect to lower risk of leaching and the possibility of regeneration, may be influenced by the chemical structure of the ligand, i.e. the stability to harsh regeneration conditions such as 1 M sodium hydroxide is dependent on the ligand structure, as well as the matrix backbone and any spacer moiety.

Therefore, with respect to criterion (c), it is a preferred that the stability (see example 8) of the solid phase matrix in 1 M NaOH is so that incubation of the matrix in 1 M NaOH in the dark at room temperature for 7 days reduces the binding efficiency at a pH in the range of one pH unit lower than the binding maximum pH to one pH unit higher than the binding maximum pH value, as determined according to the "*Standard Immunoglobulin Binding test*" described herein, with less than 50%, preferably less than 25%, compared to a corresponding untreated matrix. Preferably the reduction is less than 15%, such as at less than 10%, in particular less than 5%.

It has been found that solid phase matrices comprising a functionalised matrix backbone carrying a plurality of functional groups of the following formula

M-SP1-X-A-SP2-ACID wherein M designates the matrix backbone; SP1 designates a spacer; X designates —O—, S—, or —NH—; A designates a mono- or bicyclic optionally substituted aromatic or heteroaromatic moiety; SP2 designates an optional spacer; and ACID) designates an acidic group; with the first proviso that the molecular weight of the ligand -L is at the most 500 Dalton, are novel in themselves (specifically disclaiming 4-aminobenzoic acid disclosed in K. L. Knudsen et al, Analytical Biochemistry, vol. 201, p. 170, 1992 and WO 92/16292, which has been used for the isolation of immunoglobulins in combination with lyotropic salts, as a ligand), and that they are well suited for the isolation and/or purification of immunoglobulins as well as for the isolation and/or purification of proteins and other biomolecules in general.

It has furthermore been found that the above-mentioned solid phase matrices comprising functional groups of the formula M-SP1-X-A-SP2-ACID, are equally applicable for pH-dependent reversible binding of proteins and other biomolecules.

Thus, the present invention also provides a method for the isolation of proteins from a solution containing one or more of proteins, comprising the following operations:

a) contacting a solution containing one or more proteins having a pH in the range of 1.0 to 6.0 and a total salt content corresponding to a ionic strength of at the most 2.0 with a solid phase of the formula M-SP1-X-A-SP2-ACID, whereby at least a part of the proteins becomes bound to the solid phase matrix;

b) separating the solid phase matrix having proteins bound thereto from the solution;

c) optionally washing the solid phase matrix; and d) contacting the solid phase matrix with an eluent in order to liberate one or more of the proteins from the solid phase matrix, wherein the eluent used comprises less than 10% (v/v) of organic solvents.

The pH of the solution containing the proteins is preferably in the range of 1.0 to 6.0, such as 2.0 to 6.0, especially in the range of 3.0 to 5.5, such as 4.0 to 5.0, and the pH of the eluent is in the range of 6.0 to 11, preferably in the range of 6.0 to 9.0.

As in the method for the isolation of the immunoglobulins, the total salt content of the solution containing the proteins preferably corresponds to a ionic strength of at the most 2.0, such as in the range of 0.05 to 2.0, in particular in the range of 0.05 to 1.4, especially in the range of 0.05 to 1.0, and/or the concentration of lyotropic salts preferably is at the most 0.4 M, such as at the most 0.3 M, in particular at the most 0.2 M, especially at the most 0.1 M., Furthermore, as above, it is advantageous to use a negatively charged detergent in the contacting step (operation (a)) and/or in the washing step (operation (c)). Preferably, the washing step (operation (c)) preferably implies the use of an inorganic or organic salt buffer comprising a negatively charged detergent.

The method for the isolation of proteins and other biomolecules may be employed for a number of proteins, examples of which are proteases such as pro-enzymes, trypsins, chymotrypsins, subtilisin, pepsin, plasminogen, papain, renin, thrombin, and elastase; lipases, glucosidases; xylanases; lectins; albumins; proteins from fermentations broths; protein from milk and whey; proteins from blood, plasma, and serum; proteins from fish waste; proteins from slaughterhouse waste such as organ and tissue extracts, e.g. alkaline phosphatase from bovine intestines; and proteins from vegetable extracts such as potato, tomato, coconut, e.g. horse radish peroxidase.

Synthesis of Solid Phase Matrices

Generally a solid phase matrix may be derivatised so as to comprise covalently linked ligands according to the invention be methods know per se, e.g., activation of the solid phase matrix with a suitable reagent known per se followed by coupling of the ligand to the activated matrix, optionally incorporating a spacer SP1 between the ligand and the matrix by coupling the spacer to the activated matrix first followed by coupling the ligand to the spacer via a suitable condensation reagent or even a second activation of the spacer followed by coupling of the ligand.

The sequence and choice of reagents may depend on the actual ligand to be coupled and the solid phase material to be derivatised with consideration to, e.g., the content of reactive groups such as hydroxyl, amino, mercapto, and silanols etc. In some cases it may be preferable to activate or derivatise the ligand instead of the solid phase matrix followed by a reaction of the derivatised ligand with the solid phase matrix.

Thus, in a preferred method for of synthesising a solid phase matrix according to the invention, the solid phase matrix is first reacted with a reagent able to react with the solid phase matrix and thereby activate it for further reaction with the ligand, optionally washing away the activation reagent followed by a reaction of the activated solid phase matrix with a solution comprising the ligand and optionally followed by washing the solid phase matrix comprising the covalently immobilised ligand with one or more suitable solutions cleaning the matrix for surplus reactants.

In some cases in may be possible to combine the activation and the coupling of the ligand by mixing the two reagents and let the reactions take place in parallel. This is a great advantage as it saves costs and time as well as minimising the volume of waste water. Thus, the activation and the coupling step is preferably performed in one combined step.

Furthermore, it is a significant advantage if the activation and/or the coupling reaction can be performed without the need to add organic solvents to the reaction medium. These organic solvents are often used to solubilise the reactive reagents or to ensure that hydrolysis of reactive species are kept at a minimum. However, the use of organic solvents adds to the cost and risk of the process because of the risk of explosions, the risk of health damage, the waste problems and the relatively high cost of the solvents themselves. Thus, the activation and/or the coupling procedure is preferably performed without the addition of any organic solvent to the reaction medium.

EXAMPLES

The invention is illustrated by the following examples 1–15:

1. Derivatisation of Solid Phases
1A) Epichlorohydrin Activation of Agarose Beads
Activation of Agarose Beads from Hispanagar:
"High" Level of Activation:

Approximately 1000 ml of a 1:1 suspension of agarose beads in water (Hispanagar, 6% agarose beads, particle size 100–140 $\mu$m) was washed with demineralised water on a sintered glass funnel followed by suction draining for one minute. 700 gram of wet, but drained agarose beads were weighed into a mixture of 560 ml water and 70 ml 32,5% w/v sodium hydroxide. This suspension were then added 90 ml epichlorohydrin (ALDRICH cat.no.: E105–5) followed by gentle stirring with a paddle at room temperature (20–25° C.) for 6 hours. The agarose beads were then washed on a suction filter with approx. 20 liters of water and finally suspended in water. The activated agarose beads were found to be stable in this suspension for several weeks when stored at 4° C.

The concentration of active epoxy groups on the activated agarose beads were determined by thiosulfate titration as described in Porath, J., Låås, T., Janson, J. -C. Journal of Chromatography, vol. 103, pp. 49–69, 1975 and Sundberg, L., & Porath, J., Journal of Chromatography, vol 90, pp 87–98, 1974. The results from this titration indicated that the activated beads had a concentration of 70 $\mu$mol epoxy-groups per gram of wet, but suction drained beads, corresponding to 972 $\mu$mol/g dry matter, or 54 $\mu$mol/ml wet sedimented beads (aqueous solution).

"Low" Level of Activation:

For production of a matrix with a lower content of active epoxy groups the same procedure as described above was followed with the exemption that the reaction mixture consisted of: 200 g wet, but suction drained agarose beads, 160 ml water, 20 ml 2 M sodium hydroxide and 11.5 ml epichlorohydrin.

Thiosulfate titration indicated the presence of 21 $\mu$mol epoxy groups per gram wet, but suction drained beads, corresponding to 292 $\mu$mol/g dry matter, or 16 $\mu$mol/ml wet sedimented beads (aqueous solution).

Activation of Agarose Beads from Pharmacia and Biorad:

The same activation procedure as described above were employed for the activation of agarose beads from Pharmacia (Sepharose 4B and Sepharose 6B) and Biorad (Biogel A-5 m Gel, particle size 38–75 $\mu$m and Biogel A-15 m Gel particle size 75–150 $\mu$m).

Titration of active epoxy groups on these solid phases gave the following results:

$\mu$mol epoxy groups per gram drained beads:

| | |
|---|---|
| Sepharose 4B: | 40 |
| Sepharose 6B: | 52 |
| Biogel A 5 m Gel: | 65 |
| Biogel A 15 m Gel: | 46 |

1B) Epichlorohydrin Activation of Fractogel

Fractogel TSK HW-55 (F), particle size 32–63 $\mu$m, from MERCK (cat.no.: 14981) and Fractogel TSK HW-65 (F), particle size 32–63 $\mu$m, MERCK (cat.no.: 14984) were activated with epichlorohydrin with the same procedure as described above for agarose beads. The resulting concentration of active epoxy groups on these solid phases were 98 and 53 $\mu$mol/g of drained beads respectively.

1C) Butanedioldiglycidyl Ether Activation of Agarose Beads 100 gram 6% agarose beads from Hispanagar was washed with water on a sintered glass funnel and drained by suction for one minute. The beads were then suspended in 75 ml 0.6 M NaOH and hereafter added 75 ml 1,4-butanediol diglycidyl ether. Gentle stirring with a paddle was performed at room temperature for 18 hours whereafter the matrix was washed with water (approx. 3 litre).

Thiosulfate titration of the amount of epoxy groups incorporated into the matrix gave a content of 55 $\mu$mol/g suction drained matrix.

1D) Divinyl Sulfone Activation of Agarose Beads
Activation of Agarose Beads from Hispanagar:

Approximately 1400 ml of a 1:1 suspension of agarose beads in water (Hispanagar, 6% agarose beads, particle size 100–140 $\mu$m) was washed with demineralised water on a sintered glass funnel followed by suction draining for one minute. 700 gram of wet, but drained, agarose beads were weighed into 350 ml 0.5 M potassium phosphate buffer pH 11.5. 35 ml divinyl sulfone was added and the resulting suspension was paddle stirred at room temperature for 2 hours. The matrix was then transferred to a sintered glass funnel and washed with 20 liters of water, 5 liters of 30% ethanol in water and finally 5 liters of water. The resulting activated matrix was determined to have a content of 45 $\mu$mol active vinyl groups per gram suction drained beads as determined by the thiosulfate titration method.

1E) Coupling of Ligands to Activated Matrices
General Coupling Procedure:

All couplings of different ligands to the activated matrices mentioned in example 1 A–D were performed according to the following general procedure:

1) The activated beads were washed on a suction filter with 2–3 volumes of demineralised water. The beads were drained by slight suction on a sintered glass funnel and 20 g of wet, but drained gel were weighed into a 100 ml plastic bottle with screw cap.

2) 1 g of ligand was dissolved in 20 ml of water and titrated to pH 10.5–11.0 with 2 M sodium hydroxide (for some ligands with low solubility the pH was adjusted to pH 11.5–12.5). The resulting solution was mixed with the activated matrix. The gel was incubated with the solution by gentle mixing on a roller mixer for 18 hours at room temperature.

3) The gel was then washed with 2 liters of water.

In those instances where the ligand had poor solubility in water, a 50% ethanol solution was employed for dissolution instead followed by titration to pH 10.5–11.0 with 2 M sodium hydroxide. At the same instances the final washing with water was substituted with one washing step of 1 litre 50% ethanol followed by another washing step with 1 litre of water.

When divinyl sulfone activated agarose was used for coupling the pH of the coupling mixture was adjusted to pH 11.5 instead of 12.6.

Whenever possible the concentration of coupled ligand on the matrices was determined by elementary analysis of Carbon, Hydrogen, Nitrogen, Oxygen and Sulfur. In some instances it was furthermore possible to determined the amount of coupled ligand by acid-base titration of characteristic functional groups on the coupled ligand.

Coupling of Ligands to Epoxy-Activated 6% Agarose Beads:

The following chemical substances (ligands) were coupled to epichlorohydrin activated 6% agarose beads (Example 1-A) (Hispanagar, particle size 100–140 μm) according to the above given general coupling procedure:

2-hydroxybenzoic acid, 3-hydroxybenzoic acid, 4-hydroxybenzoic acid, 2,5-dihydroxybenzoic acid, 2-hydroxycinnamic acid, 3-hydroxycinnamic acid, 4-hydroxycinnamic acid, 3,5-di-nitrosalicylic acid, 2-hydroxy-3-methoxybenzoic acid, 3-hydroxy-4-methoxybenzoic acid, 2-hydroxy-5-methoxybenzoic acid, 4-hydroxy-3-methoxybenzoic acid, 3,5-dimethoxy-4-hydroxybenzoic acid, 2-amino-4,5-dimethoxybenzoic acid, 5-sulfosalicylic acid, 5-chlorosalicylic acid, 4-hydroxy-3,5-di-nitrobenzoic acid, 2-aminobenzoic acid, 3-aminobenzoic acid, 4-aminobenzoic acid, 2-amino-3,5 diiodobenzoic acid, 2-mercaptobenzoic acid, 2-mercaptonicotinic acid, aniline-2-sulfonic acid, 2-pyridylhydroxymethanesulfonic acid, 4-acetamidophenol, 5-mercapto-1-tetrazolacetic acid, 1-hydroxy-2-naphthoic acid, 3-hydroxy-2-naphhtoic acid, 2-hydroxy-1-naphthoic acid, 2,3-pyridine-di-carboxyl acid, 4-pyridylthioacetic acid, 2-pyrimidylthioacetic acid, 2-mercaptochinoline, imidazole, 2-mercaptoimidazole, 2-mercapto-1-methyimidazole, 3-mercapto-1,2,4-triazole, 5-mercapto-1-methyltetrazole, 2-mercaptothiazoline, 2-mercapto-5-methyl-1,3,4-thiadiazole, 2,5-di-mercapto-1,3,4-thiadiazole, benzimidazole, 2-hydroxybenzimidazole, 2-aminobenzimidazole, 2-mercaptobenzimidazole, 2-mercapto-5-nitrobenzimidazole, benzothiazole, 2-aminobenzothiazole, 2-amino-6-nitro-benzothiazole, 2-amino-6-ethoxybenzothiazole, 2-mercaptobenzthiazole, 6-ethoxy-2-mercaptobenzothiazole, 6-amino-2,5-dihydroimidazo(2,1-b)benzothiazole, 2-mercapto-benzoxazole, 2-(2-hydroxyphenyl)benzoxazole, phenol, 2-chlorophenol, 3-chlorophenol, 4-chlorophenol, 2,4,6-trimethylphenol, 2,3,5-trimethylphenol, 4-methoxyphenol, 2,6-dimethoxyphenol, 3,4,5-trimethoxyphenol, thiophenol, 4-chlorothiophenol, 2-aminothiophenol, benzyl mercaptan, 4-methoxybenzyl mercaptan, 4-methylthio-m-cresol, aniline, 2,4-dimethylaniline, 3,5-dimethoxyaniline, 3,4,5-trimethoxyaniline, 2-methylmercaptoaniline, 4-methylmercaptoaniline, 2,4,6-tri-methyl-m-phenylendiamine, 2,3-dicyanhydrochinone, 2-phenylphenol, 4-phenylphenol, 4-benzyloxyphenol, 4,4-diaminophenylsulfone, 2-hydroxypyridine, 2,3-dihydroxypyridine, 2,6-dihydroxypyridine, 2-hydroxy-5-nitropyridine, 3-cyano-4,6-dimethyl-2-hydroxypyridine, 4-hydroxy-2-mercaptopyridine, 2-mercaptopyridine, 2-aminopyridine, 4-amino-2-chlorobenzoic acid, 3-amino-4-chlorobenzoic acid, 2-amino-5-chlorobenzoic acid, 2-amino-4-chlorobenzoic acid, 2-amino-5-nitrobenzoic acid, 4-aminosalicylic acid, 5-aminosalicylic acid, 3,4-diaminobenzoic acid, 3,5-diaminobenzoic acid, 4-aminomethylbenzoic acid, 5-aminoisophthalic acid, 4-aminophthalic acid, 4-aminohippuric acid, 3-amino-1,2,4-triazole-5-carboxylic acid, 1-amino-2-naphthol-4-sulfonic acid, 2-(4-aminophenylthio)acetic acid, 2-amino-4-nitrophenol, 4-aminophenylacetic acid, 1-aminocyclohexanecarboxylic acid, 2-aminobenzylalcohol.

The ligand concentration as determined by elementary analysis on freeze-dried samples on the respective matrices generally all were in the range between 50 to 70 μmol of ligand per gram of wet, but suction drained matrix.

1F) Coupling of Ligands to Various Solid Phases

The following other solid phases: epoxy activated agarose beads from Hispanagar, activated to a low level (Example 1-A), epoxy activated agarose beads from Pharmacia and Biorad Example 1-A), epoxy activated Fractogel from Merck (Example 1-B), butanedioldiglycidyl ether activated agarose beads from Hispanagar (Example 1-C), and divinyl sulfone activated agarose beads from Hispanagar (Example 1-D) were each coupled with 2-mercapto-benzoic acid (2-MBA), 4-amino-benzoic acid (4-ABA), and 2-mercapto-benzimidazole (2-MBI).

The general coupling procedure described above in Example 1-E was followed during all couplings.

The obtained ligand concentrations were determined by elemental analysis on freeze-dried samples of the respective matrices and is calculated and given as μmol of ligand per gram of wet, but suction dried matrix. (one gram of wet, but suction dried matrix corresponds to approx. 1.1–1.3 ml sedimented beads, while the dry matter content may vary considerably more between the different type of beads.

Ligand Concentration for the Synthesised Solid Phase Matrices: (stated as μmol/g wet, but suction drained beads)

Epoxy activated agarose beads from Hispanagar, activated to a low level (Example 1-A):

| 2-MBA | 4-ABA | 2-MBI |
| --- | --- | --- |
| 18 | 20 | 20 |

Epoxy activated agarose beads from Pharmacia and Biorad (Example 1-A).:

| Matrix\Ligand | 2-MBA | 4-ABA | 2-MBI |
| --- | --- | --- | --- |
| Sepharose 4B | 37 | 40 | 38 |
| Sepharose 6B | 51 | 47 | 50 |
| Biogel A 5 m | 59 | 60 | 58 |
| Biogel A 15 m | 44 | 43 | 41 |

Epoxy activated Fractogel from Merck (Example 1-B):

| Matrix\Ligand | 2-MBA | 4-ABA | 2-MBI |
|---|---|---|---|
| Fractogel TSK HW-55 | 96 | 92 | 98 |
| Fractogel TSK HW-65 | 53 | 51 | 53 |

Butanedioldiglycidyl ether activated agarose beads from Hispanagar (Example 1-C):

| 2-MBA | 4-ABA | 2-MBI |
|---|---|---|
| 51 | 48 | 44 |

Divinyl sulfone activated agarose beads from Hispanagar (Example 1-D):

| 2-MBA | 4-ABA | 2-MBI |
|---|---|---|
| 45 | 45 | 42 |

2. Standard Immunoglobulin Binding Test

For the purpose of testing all the different solid phase materials synthesised according to example 1a standardised test, which can be reproduced any time, has been devised. The test is designed to determine the immunoglobulin binding efficiency of the different matrices under standardised conditions with respect to composition and pH of the raw material.

To ensure maximal relevancy of the test for isolation of monoclonal antibodies from dilute cell culture supernatants we have simulated the conditions used for culturing hybridoma cells by mixing a typical cell culture media with fetal calf serum and added purified mouse immunoglobulin to this "artificial culture supernatant." All reagents are standard reagents and commercially available.

Definition of "Artificial Culture Supernatant":

For 250 ml solution:

236.5 ml cell culture growth medium, DMEM (Imperial, UK, cat.no.: 7-385-14)

12.5 ml fetal calf serum (Life Technologies, Denmark, cat.no.: 10106-060)

1,0 ml purified polyclonal murine IgG (Sigma, USA, cat.no.: I-8765, 10 mg/ml)

0.244 g sodium azide (Sigma, USA, cat.no.: S-2002), resulting in a solution containing: 40 µg murine IgG/ml, 5% fetal calf serum, and 15 mM sodium azide, and having a pH of approx. 8.0.

This solution was shown to be stable at 4° C. for several weeks without any deterioration of the immunoglobulins.

Standard Procedure:

1) Approximately 100 mg of the matrix to be tested is washed with 10 ml demineralised water on a sintered glass funnel followed by suction draining for 60 seconds. 100 mg of wet (drained) solid phase matrix is weighed into a 3.0 ml test tube and 2.50 ml "artificial culture supernatant" having the pH value at which the matrix is to be tested is added. The test tube is closed with a stopper, and the suspension is incubated on a roller mixer for 2 hours at room temperature (20–25° C.). The test tube is then centrifuged for 5 min. at 2000 RPM in order to sediment the matrix. The supernatant is then isolated from the solid-phase matrix by pipetting into a separate test tube, avoiding the carry-over of any matrix particles. Following this a determination of the concentration of non-bound immunoglobulin in the supernatant is performed by single radial immunodiffusion (as described in D. Catty and C Raykundalia "Antibodies—a practical approach" Vol I, pp. 137–168, 1988) using rabbit anti mouse immunoglobulins as the precipitating antibody (DAKO, Denmark, cat.no.:Z109).

The percentage of mouse immunoglobulin bound to the matrix is then calculated according to the following formula:

Percentage bound=(1-(conc. supernatant/conc. starting material))× 100%

The precision of this method is better than +/−5%.

2A) Screening for High Immunoglobulin Binding Efficiency

The above described standard procedure for testing the binding efficiency was used for testing a broad range of different solid phase matrices based on epichlorohydrin activated 6% agarose beads from Hispanagar and synthesised according to example 1A and 1E.

The results of the binding test performed at pH 4.5 and pH 7.0 respectively is presented in the Table I below:

TABLE I

| Ligand | Capacity at pH 4.5 | Capacity at pH 7.0 |
|---|---|---|
| 2-hydroxybenzoic acid | 0 | 0 |
| 3-hydroxybenzoic acid | 0 | 30 |
| 4-hydroxybenzoic acid | 0 | 0 |
| 2,5-dihydroxybenzoic acid | 60 | 0 |
| 2-hydroxycinnamic acid | 20 | 0 |
| 3-hydroxycinnamic acid | 80 | 0 |
| 4-hydroxycinnamic acid | 40 | 0 |
| 3,5-dinitrosalicylic acid | 0 | 0 |
| 2-hydroxy-3-methoxybenzoic acid | 0 | 0 |
| 3-hydroxy-4-methoxybenzoic acid | 40 | 0 |
| 2-hydroxy-5-methoxybenzoic acid | 0 | 0 |
| 4-hydroxy-3-methoxybenzoic acid | 0 | 0 |
| 3,5-dimethoxy-4-hydroxybenzoic acid | 0 | 30 |
| 2-amino-4,5-dimethoxybenzoic acid | 20 | 0 |
| 5-sulfosalicylic acid | 0 | 0 |
| 5-chlorosalicylic acid | 0 | 0 |
| 4-hydroxy-3,5-dinitrobenzoic acid | 0 | 0 |
| 2-aminobenzoic acid | 80 | 0 |
| 3-aminobenzoic acid | 100 | 0 |
| 4-aminobenzoic acid | 90 | 0 |
| 2-amino-3,5-diiodobenzoic acid | 0 | 0 |
| 2-mercaptobenzoic acid | 100 | 0 |
| 2-mercaptonicotinic acid | 100 | 0 |
| aniline-2-sulfonic acid | 0 | 0 |
| 2-pyridylhydroxymethansulfonic acid | 0 | 0 |
| 4-acetamidophenol | 0 | 0 |
| 5-mercapto-1-tetrazole acetic acid | 70 | 0 |
| 1-hydroxy-2-naphthoic acid | 0 | 0 |
| 3-hydroxy-2-naphthoic acid | 0 | 0 |
| 2-hydroxy-1-naphthoic acid | 60 | 0 |
| pyridine-2,3-dicarboxylic acid | 0 | 0 |
| 4-pyridylthioacetic acid | 0 | 0 |
| 2-pyrimidylthioacetic acid | 0 | 0 |
| 2-mercaptochinoline | 80 | 60 |
| imidazole | 0 | 0 |
| 2-mercaptoimidazole | 0 | 0 |
| 2-mercapto-1-methylimidazole | 20 | 0 |
| 3-mercapto-1,2,4-triazole | 0 | 0 |
| 5-mercapto-1-methyltetrazole | 0 | 0 |
| 2-mercaptothiazoline | 20 | 0 |
| 2-mercapto-5-methyl-1,3,4-thiadiazole | 0 | 20 |
| 2,5-dimercapto-1,3,4-thiadiazole | 100 | 20 |
| benzimidazole | 0 | 0 |
| 2-hydroxybenzimidazole | 0 | 0 |
| 2-aminobenzimidazole | 40 | 20 |

TABLE I-continued

| Ligand | Capacity at pH 4.5 | Capacity at pH 7.0 |
|---|---|---|
| 2-mercaptobenzimidazole | 70 | 70 |
| 2-mercapto-5-nitrobenzimidazole | 80 | 90 |
| benzothiazole | 0 | 0 |
| 2-aminobenzothiazole | 20 | 0 |
| 2-amino-6-nitro-benzothiazole | 80 | 60 |
| 2-amino-6-ethoxy-benzothiazole | 0 | 0 |
| 2-mercaptobenzothiazole | 70 | 60 |
| 6-ethoxy-2-mercaptobenzothiazole | 20 | 40 |
| 6-amino-2,5-dihydroimidazo(2,1-b)benzothiazole | 0 | 20 |
| 2-mercaptobenzoxazole | 80 | 60 |
| 2-(2-hydroxyphenyl)benzoxazole | 0 | 0 |
| phenol | 0 | 0 |
| 2-chlorophenol | 0 | 0 |
| 3-chlorophenol | 0 | 0 |
| 4-chlorophenol | 0 | 20 |
| 2,4,6-trimethylphenol | 20 | 0 |
| 2,3,5-trimethylphenol | 20 | 20 |
| 2,6-dimethoxyphenol | 0 | 0 |
| 3,4,5-trimethoxyphenol | 0 | 0 |
| thiophenol | 70 | 60 |
| 4-chlorothiophenol | 100 | 70 |
| 2-aminothiophenol | 70 | 50 |
| benzyl mercaptan | 0 | 0 |
| aniline | 20 | 20 |
| 2,4-dimethylaniline | 0 | 0 |
| 3,4,5-trimethoxyaniline | 0 | 0 |
| 2-methylmercaptoaniline | 60 | 0 |
| 2,4,6-tri-methyl-m-phenylendiamine | 20 | 0 |
| 2,3-dicyanhydrochinone | 20 | 0 |
| 2-phenylphenol | 0 | 0 |
| 4-phenylphenol | 20 | 20 |
| 4-benzyloxyphenol | 0 | 0 |
| 1,4-diaminophenylsulfone | 20 | 0 |
| 2-hydroxypyridine | 0 | 0 |
| 2,3-dihydroxypyridine | 20 | 0 |
| 4-hydroxy-2-mercaptopyridine | 60 | 40 |
| 4-amino-2-chlorobenzoic acid | 0 | 40 |
| 3-amino-4-chlorobenzoic acid | 0 | 0 |
| 2-amino-5-chlorobenzoic acid | 80 | 0 |
| 2-amino-4-chlorobenzoic acid | 40 | 0 |
| 2-amino-5-nitrobenzoic acid | 0 | 0 |
| 4-aminosalicylic acid | 80 | 20 |
| 5-aminosalicylic acid | 80 | 30 |
| 3,4-diaminobenzoic acid | 80 | 0 |
| 3,5-diaminobenzoic acid | 60 | 0 |
| 4-aminomethylbenzoic acid | 0 | 0 |
| 5-aminoisophthalic acid | 60 | 20 |
| 4-aminophthalic acid | 60 | 20 |
| 4-aminohippuric acid | 0 | 20 |
| 3-amino-1,2,4-triazol-5-carboxylic acid | 0 | 20 |
| 1-amino-2-naphthol-4-sulfonic acid | 80 | 20 |
| 2-(4-aminophenylthio)acetic acid | 80 | 0 |
| 2-amino-4-nitrophenol | 80 | 20 |
| 4-aminophenylacetic acid | 0 | 0 |
| 1-aminocyclohexancarboxylic acid (reference) | 0 | 0 |
| 2-aminobenzylalcohol | 20 | 0 |

As can be seen from the table some ligands do not bind the immunoglobulin at all while others show very efficient binding in the range of 80–100% and still other ligands show intermediate binding efficiencies in the range of 30–60%.

As can be seen from the result from 1-aminocyclohexancarboxylic acid (reference), an aromatic or heteroaromatic moiety seems to be required for efficient binding.

3. Monoclonal Antibody Array Binding Test

The following example illustrates the differences in binding efficiency between prior art solid phase matrices and solid phase matrices according to the invention for immunoglobulin purification.

For the comparative study 7 different cell lines capable of producing 7 different monoclonal antibodies were acquired from the American Type Culture Collection (ATCC) and propagated according to a standard procedure as described below. Hereafter the binding efficiency of each monoclonal antibody was tested with each of the solid phases: protein A agarose (prior art matrix), Avidchrom (prior art matrix) and epoxy-linked 2-mercapto-benzoic acid agarose, 4-amino-benzoic acid agarose and 2-mercapto-benzimidazole agarose.

The study was designed to determine the antibody binding efficiency during batch incubation of the 5 different solid phases with culture supernatants from the 7 different commercially available cell lines.

Monoclonal Antibodies:

Cell lines: The following seven cell lines available from the American Type Culture Collection were included in the standardised set-up:

| ATCC cat no. | Immunoglobulin type produced |
|---|---|
| HB 134 | Mouse $IgG_1$ |
| HB 8279 | Mouse $IgG_{2b}$ |
| HB 8445 | Mouse $IgG_8$ |
| CRL 1852 | Mouse $IgG_1$ |
| HB 121 | Mouse $IgG_{2a}$ |
| HB 8857 | Rat $IgG_1$ |
| CRL 8018 | Mouse IgM |

Cultures: The monoclonal antibody culture supernatants used in the study were produced by culture of the corresponding mouse and rat hybridoma cells in a medium containing fetal calf serum (RPMI-X, Medicult, Denmark cat.no. 20230500+5% fetal calf serum, Imperial, United Kingdom, cat.no. 83041). The methodology used for culturing the five cell lines is well established in the prior art and described in G. Brown and N. R. Ling "Antibodies—a practical approach" Vol I, pp.81–104, 1988). After 3 weeks of culture the cells were removed by centrifugation and the supernatant filtered to remove any remaining particles. The concentration of monoclonal antibody in the five different culture supernatants were determined by single radial immunodiffusion (as described in D. Catty and C Raykundalia "Antibodies—a practical approach" Vol I, pp. 137–168, 1988) using rabbit anti mouse immunoglobulins and rabbit anti rat immunoglobulins as the precipitating antibodies (DAKO, Denmark, cat.no.:Z109 and Z147) and found to be in the range of 30 to 60 $\mu g/ml$ for all clones. Hereafter the content of monoclonal antibody in each culture supernatant was standardised by dilution to reach a final concentration of 30 $\mu g/ml$. To ensure similar conditions for all the supernatants the dilution was performed with culture medium including 5% fetal calf serum.

Solid phases: Protein A agarose from Repligen Corporation, USA, cat no.:IPA-300. lot no.: RN 2917; Avidchrom from Unisyn Technologies, USA, cat. no.: 3100-0025, lot no.: 96-0404-1; 2-mercapto-benzoic acid agarose, 4-amino-benzoic acid agarose and 2-mercapto-benzimidazole agarose were based on epichlorohydrin activated 6% agarose beads from Hispanagar, Spain and synthesised as described in example 1A and 1E. The ligand concentrations were measured by elemental analysis and found to be 65, 69 and 69 $\mu$moles/gram wet, but drained matrix respectively (corresponding to 903, 958 and 958 $\mu$moles/g dry matter as measured by elemental analysis on freeze dried samples).

The five different solid phase matrices were tested for their monoclonal antibody binding efficiency by incubating them with the 7 different monoclonal antibody supernatants (standardised at 30 μg antibody/ml) according to the following procedure:

Standard Procedure for the "Monoclonal Antibody Array Binding Test":

Approximately 100 mg of the matrix to be tested is washed with 10 ml demineralised water on a sintered glass funnel followed by suction draining for 60 seconds. 100 mg of wet (drained) solid phase matrix is weighed into a 3.0 ml test tube and 4.0 ml monoclonal antibody culture supernatant adjusted to the pH value at which the matrix is to be tested is added. The test tube is closed with a stopper, and the suspension is incubated on a roller mixer for 2 hours at room temperature (20–25° C.). The test tube is then centrifuged for 5 min. at 2000 RPM in order to sediment the matrix. The supernatant is then isolated from the solid phase matrix by pipetting into a separate test tube, avoiding the carry-over of any matrix particles. Following this a determination of the concentration of non-bound immunoglobulin in the supernatant is performed by single radial immunodiffusion.

The percentage of monoclonal antibody bound to the matrix is then calculated according to the following formula:

Percentage bound=(1-(conc. in supernatant/30 μg/ml))×100%

The precision of this method is better than +/−5%.

pH Adjustments to Culture Supernatants for the Different Solid Phases:

Protein A agarose: The monoclonal antibody culture supernatants were adjusted to pH 8.2 by the addition TRIS/HCl to a final TRIS concentration of 0.05 M.

Avidchrom: The monoclonal antibody culture supernatants were adjusted to pH 7.4 by addition of potassium hydrogen phosphate/HCl to a final phosphate concentration of 0.05 M.

2-mercapto-benzoic acid and 4-amino-benzoic acid agarose: The monoclonal antibody culture supernatants were adjusted to pH 4.5 by addition of acetic acid/sodium hydroxide to a final acetic acid concentration of 0.05 M.

2-mercapto-benzimidazole: The monoclonal antibody culture supernatants were adjusted to pH 7.0 by addition of potassium hydrogen phosphate/HCl to a final phosphate concentration of 0.05 M.

| | Binding efficiency % | | | | |
|---|---|---|---|---|---|
| | Adsorbent ATCC cat.no. Subtype | | | | |
| Clone | 2-MBA | 4-ABA | 2-MBI | Protein A | Avidchrom |
| HB 134 Mouse IgG$_1$ | 100 | 100 | 75 | 0 | 50 |
| HB 8445 Mouse IgG$_3$ | 100 | 100 | 95 | 80 | 80 |
| CRL 1852 Mouse IgG$_1$ | 100 | 100 | 55 | 20 | 40 |
| HB 8279 Mouse IgG$_{2b}$ | 95 | 95 | 75 | 70 | 50 |
| HB 121 Mouse IgG$_{2a}$ | 90 | 100 | 85 | 100 | 40 |
| HB 8857 Rat IgG$_1$ | 95 | 100 | 95 | 95 | 100 |
| CRL 8018 Mouse IgM | 85 | 60 | 45 | 0 | 10 |
| Average binding efficiency % | 95 | 94 | 75 | 52 | 53 |

2-MBA: 2-mercapto-benzoic acid agarose (epichlorohydrin)
4-ABA: 4-amino-benzoic acid agarose (epichlorohydrin)
2-MBI: 2-mercapto-benzimidazole agarose (epichlorohydrin)

As can be seen from the table the solid phase matrices according to the invention i.e. 2-mercapto-benzoic acid agarose, 4-amino-benzoic acid agarose and 2-mercapto-benzimidazole agarose exhibits a very constant high binding efficiency with the different clones (typically in the range of 50–100% binding), while the prior art solid phase matrices, protein A agarose and Avidchrom, exhibits much more varying binding efficiency (in the range from 0–100% binding). The average binding efficiency has been calculated for each adsorbent and it is also from these data seen that the prior art adsorbents with average binding efficiencies of 52 and 53% are significantly less efficient than the adsorbents according to the invention which have average binding efficiencies in the range from 75–95%.

4. 2-Mercaptobenzoic Acid as the Ligand

Isolation of Immunoglobulins under Different Binding and Washing Conditions

As is indicated from the results in table I 2-mercaptobenzoic acid seems to be a very interesting ligand for isolation and purification of monoclonal antibodies from dilute culture supernatants. Further studies of this solid phase matrix employing the "artificial culture supernatant" as described in example 2 was therefore performed with the aim of establishing the optimal binding and washing conditions so as to achieve the maximal binding capacity as well as yield and purity of the antibody in the eluate.

2-mercapto-benzoic acid agarose was based on epichlorohydrin activated 6% agarose beads from Hispanagar and synthesised as described in example 1A and 1E. The ligand concentration was measured by two different methods and found to be 65 μmol/g wet, but drained matrix as determined by elementary analysis and 60 μmol/g as determined by acid-base titration of the immobilised benzoic acid part of the ligand.

Generally the experiments were performed according to the following procedure:

1) A small aliquot of 2-mercaptobenzoic acid agarose was washed with water (all water unless otherwise stated had the quality of Milli Q water) on a sintered glass funnel by gentle suction followed by draining of the interstitial water by light suction for one minute.

2) 0.4 gram of wet, but drained matrix was then weighed into a test tube followed by the addition of 10 ml "artificial culture supernatant" having a specific pH-value for that particular experiment. With or without any further additives the suspension was hereafter incubated on a roller mixer for two hours at room temperature to ensure efficient binding of the immunoglobulin.

3) Following incubation the matrix was transferred to a column with a 5 mm inner diameter, drained for excess "artificial culture medium" and washed according to a scheme specific for the particular experiment. Washing was performed by adding 4×4 ml washing buffer to the column and collecting the run-through from the column in one fraction.

4) The final elution of bound immunoglobulin was performed with a specific elution buffer by addition of 4×2.5 ml buffer to the column and collecting the eluate in one fraction. No pumps were employed in the experiments, all columns were run by gravity (at an approximate flow rate of 0.5–1.0 ml/min).

5) Analyses were performed to determine the relative distribution of immunoglobulin between the non-bound fraction in the supernatant after binding, the washing fraction(s) and the eluate. This was done by single radial immunodiffusion (as described in D. Catty and C Raykundaha "Antibodies—a practical approach" Vol I, pp. 137–168, 1988) using rabbit anti mouse immunoglobulins as the precipitating antibody (DAKO A/S, Denmark, Cat.no.: Z 109).

The binding capacity was then calculated from the amount of non-bound immunoglobulin present in the supernatant and expressed as a percentage of the total amount added to the matrix in the raw material.

The yield was calculated as the percentage of the added immunoglobulin found in the eluate fraction (i.e. a yield of 100% is equal to the presence of 1 mg IgG in the eluate).

The purity of the eluted immunoglobulin was analysed by SDS-PAGE (sodium dodecyl sulfate polyacrylamide electrophoresis) under reducing conditions followed by staining of the protein bands with coomassie brilliant blue. (Precast gel 4–20% tris-glycine, 1 mm cat.no.: EC6025, running 1 hour at 30 mA; tris-glycine SDS running buffer cat.no.: LC2675; tris-glycine sample buffer cat.no.: LC2676; coomassie staining kit LC6025 all chemicals from Novex, USA)

The degree of purity as expressed in percent of the total protein contents was determined by scanning and image processing of the coomassie stained and dried polyacrylamide gel. For this purpose we employed the CREAM system available from Kem-En-Tec A/S, Denmark (cat no.: 6010+ 6050).

4A) The Effect of Performing Binding at Different pH-Values

The following experiment was performed to establish the pH-range in which the 2-mercapto-benzoic acid matrix would bind immunoglobulins efficiently from the "artificial culture supernatant". As was shown in Table I example 2, this matrix binds 100% at pH 4.5 and 0% at pH 7.0. In this experiment the binding efficiency, yield and purity of the eluate is determined when binding is performed in the pH range 3.0–6.5. In all instances the washing buffer used was 10 mM citric acid buffer adjusted to the same pH as the binding pH with 1 M sodium hydroxide. The elution buffer used was in all instances 0.05 M boric acid/NaOH+0.5 M sodium chloride pH 8.6

Results

| pH of binding | percent binding | Yield (%) | Purity (%) |
|---|---|---|---|
| 3.0 | 100 | 90 | <5 |
| 3.5 | 100 | 95 | <5 |
| 4.0 | 100 | 100 | <5 |
| 4.5 | 100 | 100 | <5 |
| 5.0 | 95 | 95 | 5 |
| 5.5 | 40 | 40 | 10 |
| 6.0 | 0 | 0 | — |
| 6.5 | 0 | 0 | — |

As can be seen from the table efficient binding is achieved at pH-values below 6.0 reaching 100% at pH 4.5. At the same time there is an indication that a relatively higher purity may be obtained if the binding step is performed at a higher pH than 4.5.

4B) The Effect of Different Washing Procedures/pH in Washing Buffer

A series of tests were performed with the aim of optimising the purity of the eluate while maintaining the yield at a high level. For this purpose a range of different washing procedures were tested. All tests were performed with pH 4.5 as the pH of binding and all eluates were performed with 0.05 M boric acid/NaOH+0.5 M NaCl pH 8.6.

Results

| Washing buffer: | purity (%) | yield (%) |
|---|---|---|
| 10 mM citric acid/NaOH pH 4.5 | <5 | 100 |
| 10 mM citric acid/NaOH pH 5.5 | 5 | 95 |
| 10 mM citric acid/NaOH pH 6.5 | 15 | 80 |
| 20 mM TRIS/HCl pH 7.5 | 20 | 70 |
| 20 mM TRIS/HCl pH 8.5 | 20 | 60 |

As can be seen from the table the purity of the eluate may be increased by washing with a higher pH, but an increase in pH above pH 5.5 decreases the yield significantly.

4C) The Effect of Different Washing Procedures/Lyotropic Salts at High pH

Experiments were performed as described in 3 B except that a series of washing buffers containing different lyotropic salts at pH 8.0 were tested for their ability to improve the purity of the eluate without significantly decreasing the yield.

Results

| Washing buffer: | purity (%) | yield (%) |
|---|---|---|
| 0.7 M ammonium sulfate/NaOH pH 8.0 | ND | <10 |
| 0.9 M ammonium sulfate/NaOH pH 8.0 | 25 | 30 |
| 1.0 M ammonium sulfate/NaOH pH 8.0 | 25 | 80 |
| 1.1 M ammonium sulfate/NaOH pH 8.0 | 20 | 95 |
| 1.3 M ammonium sulfate/NaOH pH 8.0 | 20 | 95 |
| 0.8 M potassium phosphate pH 8.0 | 20 | 95 |
| 1.0 M potassium phosphate pH 8.0 | 15 | 95 |
| 0.9 M sodium sulfate/NaOH +0.05 M sodium bicarbonate pH 8.0 | 20 | 95 |
| 1.0 M sodium sulfate/NaOH +0.05 M sodium bicarbonate pH 8.0 | 20 | 95 |
| 1.0 M sodium chloride +0.05 M potassium phosphate pH 8.0 | ND | 0 |
| 2.0 M sodium chloride +0.05 M potassium phosphate pH 8.0 | ND | 0 |
| 4.0 M sodium chloride +0.05 M potassium phosphate pH 8.0 | 20 | 80 |

The results indicate that the presence of lyotropic salts in the washing buffer combined with a higher pH than the binding pH may increase the purity of the eluate significantly without decreasing the yield. It is also evident that a certain concentration of the lyotropic salt is necessary to obtain this result. Too low concentrations results in loss of immunoglobulin in the washing fraction, resulting in very low yields. As can be seen the necessary concentration is dependent on the nature of the lyotropic salt, e.g. ammonium sulfate which is considered a strongly lyotropic salts according to the Hofmeister series (see Gagnon cited herein) need only to have a concentration of about 1.0–1.1 M to ensure a high yield in the eluate, while sodium chloride, which is considered a poor weakly lyotropic salt according to the Hofmeister series, needs to have a concentration of about 4 M before the yield is increasing to an acceptable level.

4D) The Effect of Different Washing Procedures/Different Additives

The effect of adding detergents and other additives to the washing buffer was investigated in tests performed as described above (example 4B and 4C)

Results

| Washing buffer: | purity (%) | yield (%) |
|---|---|---|
| 0.01 M citric acid/NaOH pH 6.5 +3 mg/ml octyl sulfate | 50 | 80 |
| 0.01 M citric acid/NaOH pH 5.8 +0.05 mg/ml bromophenol blue | 70 | 90 |
| 1.0 M ammonium sulfate/NaOH pH 7.5 +10 mg/ml octane sulfonic acid | 80 | 80 |
| 1.0 M ammonium sulfate/NaOH pH 8.0 +5 mg/ml sodium laurylsarcosinate | 60 | 80 |
| 1.0 M ammonium sulfate/NaOH pH 8.0 +5 mg/ml octane sulfonic acid +5 mg/ml sodium laurylsarcocinate | 80 | 70 |
| 0.9 M potassium phosphate pH 9.2 +5 mg/ml octane sulfonic acid | 80 | 80 |
| 0.9 M potassium phosphate pH 9.2 +5 mg/ml hexane sulfonic acid | 60 | 90 |
| 1.0 M ammonium sulfate/NaOH pH 8.0 +5 mg/ml tween 20 | 25 | 90 |
| 1.0 M ammonium sulfate/NaOH pH 8.0 +5 mg/ml pluronic F68 | 25 | 80 |

The results from these experiments clearly indicate the positive effect on the purity of the eluate obtained by washing the matrix with buffers containing a negatively charged detergent (e.g. octane sulfonic acid, hexane sulfonic acid, octyl sulfate and sodium laurylsarcosinate), while the addition of uncharged detergents such as Tween 20 and pluronic F-68 seems to have little or no effect on the purity of the eluted immunoglobulin. Likewise it is shown that bromophenol blue, which is known to have a high affinity for binding to albumin (an unwanted impurity) also has a significant effect on the purity without compromising the yield of product. Furthermore the obtained effect seems to be independent of whether the washing buffer comprises high concentrations of lyotropic salts or not as well as the choice of lyotropic salt used, if present.

4E) The Effect of Different Additives During Binding

The following experiments were performed to investigate the effect on purity and yield of the addition of different detergents and other chemical substances to the "artificial culture supernatant" during the incubation with the 2-mercapto-benzoic acid agarose. For all tests the pH of binding was pH 5.0, the washing buffer used was 1.1 M ammonium sulfate/NaOH pH 8.0 and the elution buffer was 0.05 M boric acid/NaOH+0.5 M sodium chloride pH 8.6. The experiments were otherwise performed as described in the general procedure above.
Results

| Substance added: | purity (%) | yield (%) |
|---|---|---|
| None | 25 | 95 |
| 5 mg/ml Tween 20 | 30 | 80 |
| 10 mg/ml benzoic acid | 25 | 50 |
| 5 mg/ml 1-octyl-2-pyrrolidone | 20 | 80 |
| 5 mg/ml N-octanoyl-N-methylglucamine | 20 | 80 |
| 1 mg/ml lauryl sulfobetaine | 20 | 80 |
| 5 mg/ml lauryl sulfobetaine | ND | 0 |
| 5 mg/ml suberic acid | 25 | 80 |
| 5 mg/ml sebacic acid | 25 | 80 |
| 5 mg/ml octane sulfonic acid | 25 | 90 |
| 5 mg/ml caproic acid | 60 | 90 |
| 5 mg/ml caprylic acid | 70 | 80 |
| 0.5 mg/ml sodium laurylsarcosinate | 70 | 90 |
| 1.0 mg/ml sodium laurylsarcosinate | 85 | 90 |
| 2.0 mg/ml sodium laurylsarcosinate | 90 | 70 |
| 1 mg/ml bromophenol blue | 80 | 90 |

The results indicate that the addition of certain negatively charged detergents (or amphophilic substances) to the "artificial culture supernatant" prior to the incubation with 2-mercapto-benzoic acid agarose has a significant influence on the final purity of the eluate. This is for example the case for substances such as caproic and caprylic acid as well as lauryl sarcosinate, while other negatively charged substances such as benzoic acid, lauryl sulfobetaine, suberic acid, sebacic acid and octane sulfonic acid seems to have very little effect in the concentrations tested. It is also noted that the neutral detergents Tween 20 and the positive detergent 1-octyl-N-methylglucamine seems to have no effect either.

4F) The Effect of Different Washing Buffers in Combination with the Addition of Sodium Laurylsarcosinate to the Raw Material The following example demonstrates the effect of combining the addition of a negatively charged detergent to the raw material with a series of different washing buffer compositions. In all experiments there is added 1 mg/ml sodium lauryl sarcosinate to the "artificial culture supernatant" prior to mixing with the 2-mercapto-benzoic acid agarose, pH1 of binding were pH 5.0 and the elution buffer were in all cases 0.05 M boric acid/NaOH+0.5 M sodium chloride pH 8.6. Otherwise the general procedure described above was followed.
Results

| Washing buffer: | purity (%) | yield (%) |
|---|---|---|
| water | 45 | 90 |
| 0.001 M sodium citrate pH 6.0 | 45 | 90 |
| 0.001 M sodium citrate pH 6.5 | 50 | 90 |
| 0.001 M sodium citrate pH 7.0 | 50 | 90 |
| 0.001 M potassium phosphate pH 7.5 | 50 | 90 |
| 0.001 M sodium citrate pH 6.5 +5% monopropylene glycol | 50 | 80 |
| 0.001 M sodium citrate pH 6.5 +20% monopropylene glycol | 45 | 95 |
| 1.0 M ammonium sulfate/NaOH pH 7.5 | 60 | 85 |
| 1.0 M ammonium sulfate/NaOH pH 7.0 | 60 | 90 |
| 0.9 M ammonium sulfate/NaOH pH 7.0 | 60 | 75 |

5. 4-Amino Acid as the Ligand
Isolation of Monoclonal Antibodies under Different Conditions 4-amino-benzoic acid is another aromatic acid according to the invention that seems to be very interesting for use in monoclonal antibody purification (table I, example 2). The following tests demonstrates the influence of different binding and washing conditions on the performance of 4-amino-benzoic acid agarose based on 6% agarose from Hispanagar and synthesised according to example 1A and 1E. The matrix used was analysed by elemental analysis and determined to have a content of 69 $\mu$mol 4-amino-benzoic acid groups per ml wet, but drained matrix.

The tests were performed as described in the general procedure in example 4.

5A) The Effect of Performing Binding at Different pH-Values

The following experiment was performed to establish the pH-range in which the 4-amino-benzoic acid matrix would bind immunoglobulins efficiently from the "artificial culture supernatant". As was shown in Table I example 2, this matrix binds 90% at pH 4.5 and 0% at pH 7.0. In this experiment the binding efficiency, yield and purity of the eluate is determined when binding is performed in the pH-range 4.0–6.5. In all instances the washing buffer used was 10 mM citric acid buffer adjusted to the same pH as the binding pH with 1 M sodium hydroxide. The elution buffer used was in all instances 0.05 M boric acid/NaOH+0.5 M sodium chloride pH 8.6

Results

| pH of binding | percent binding | Yield (%) | Purity (%) |
|---|---|---|---|
| 4.0 | 100 | 90 | 10 |
| 4.5 | 90 | 95 | 10 |
| 5.0 | 60 | 55 | 20 |
| 5.5 | 20 | ND | ND |
| 6.0 | 0 | ND | ND |
| 6.5 | 0 | ND | ND |

As can be seen from the table efficient binding is achieved at pH-values below 5.5 reaching 90% at pH 4.5. At the same time there is an indication that a relatively higher purity may be obtained if the binding step is performed at a higher pH than 4.5.

5B) The Effect of Different Washing Procedures/pH in Washing Buffer

A series of tests were performed with the aim of optimising the purity of the eluate while maintaining the yield at a high level. For this purpose a range of different washing procedures were tested. All tests were performed with pH 4.6 as the pH of binding and all eluates were performed with 0.05 M boric acid/NaOH+0.5 M NaCl pH 8.6.

Results

| Washing buffer: | purity (%) | yield (%) |
|---|---|---|
| 10 mM citric acid/NaOH pH 4.5 | 10 | 90 |
| 10 mM citric acid/NaOH pH 5.5 | 25 | 90 |
| 10 mM citric acid/NaOH pH 6.0 | 60 | 80 |
| 10 mM citric acid/NaOH pH 6.5 | 75 | 55 |

As can be seen from the table the purity of the eluate may be increased by washing with a higher pH, but an increase in pH above pH 6.0 decreases the yield significantly.

6. 2-Mercapto-nicotinic Acid

Isolation of Monoclonal Antibodies under Different Conditions 2-mercapto-nicotinic acid is another aromatic acid according to the invention that seems to be very interesting for use in monoclonal antibody purification (table I, example 2). The following tests demonstrates the influence of different binding and washing conditions on the performance of 2-mercapto-nicotinic acid agarose based on epichlorohydrin activated 6% agarose from Hispanagar and synthesised according to example 1A and 1E. The matrix used was analysed by elemental analysis and determined to have a content of 63 $\mu$mol 2-mercapto-nicotinic acid groups per ml wet, but drained matrix.

The tests were performed as described in the general procedure in example 4.

In these two tests the effect of varying binding pH on yield and purity of the resulting eluate was investigated while keeping washing and elution conditions constant. In both instances the washing buffer was 1.1 M ammonium sulfate/NaOH pH 8.0+5 mg/ml octyl sulfate and the elution buffer was 0.05 M boric acid/NaOH pH 8.6+0.5 M sodium chloride.

The "artificial culture supernatant" was adjusted to pH 4.5 and 5.0 with 1 M hydrochloric acid respectively and no further additions were made.

Results

| Binding pH | Yield, % | Purity, % |
|---|---|---|
| 4.6 | 85 | 80 |
| 5.0 | 75 | 95 |

As can be seen this matrix provides an excellent yield of immunoglobulin in the eluate at both binding pH-values while the purity of the eluted immunoglobulin is significantly increased by raising the binding pH from pH 4.5 to pH 5.0.

Effect of Adding Sodium Lauryl Sarcosunte to the Raw Material

In the following tests the effect of adding different amounts of sodium lauryl sarcosinate to the "artificial culture supernatant" at two different binding pH-values is investigated. In all tests the washing buffer used was 1.1 M ammonium sulfate/NaOH pH 7.5 and the elution buffer was 0.05 M boric acid/NaOH pH 8.6+0.5 M sodium chloride.

Prior to mixing with the solid phase matrix the "artificial culture supernatant" was added sodium lauryl sarcosinate to three different concentrations and then adjusted to pH 4.5 and 5.0 with 1 M hydrochloric acid respectively.

Results

Binding at pH 4.5

| Concentration of SLS, mg/ml | Yield, % | Purity, % |
|---|---|---|
| Binding at pH 4.5 | | |
| 0.5 | 90 | 50 |
| 1.0 | 90 | 65 |
| 1.5 | 65 | 85 |
| Binding at pH 5.0: | | |
| 0.5 | 90 | 50 |
| 1.0 | 90 | 85 |
| 1.5 | 40 | >95 |

SLS = Sodium Lauryl Sarcosinate

7. 2-Mercaptobenzimidazole

Isolation of Monoclonal Antibodies

As is indicated in Table I, 2-mercaptobenzimidazole represents another very interesting group of ligands (the benzimidazoles, benzoxazoles and benzothiazoles) for immunoglobulin isolation. The following example illustrates the application of this ligand for binding and isolation of immunoglobulins from the "artificial culture supernatant" described in example 2.

2-mercapto-benzimidazole agarose was based on epichlorohydrin activated 6% agarose beads from Hispanagar and synthesised as described in example 1A and 1E. The ligand concentration was measured by elemental analysis and found to be 69 $\mu$mol/g wet, but drained matrix.

In the following tests the yield and purity obtained by incubation of the 2-mercaptobenzimidazole agarose with "artificial culture supernatant" containing different concentrations of added polyvinyl pyrrolidone is determined by following the general procedure described in example 4. The pH of binding was adjusted to pH 7.5 with hydrochloric acid, the washing buffer was 0.01 M potassium phosphate+0.5 M sodium chloride pH 7.5 and the elution buffer was 0.01 M citric acid/NaOH pH 3.5.

Results

| Concentration of PVP, mg/ml | Yield, % | Purity, % |
|---|---|---|
| 0.0 | 95 | 25 |
| 0.5 | 80 | 70 |
| 1.0 | 70 | 80 |
| 2.0 | 40 | 90 |
| 4.0 | 5 | ND |

PVP: polyvinyl pyrrolidone

The results indicate that 2-mercapto-benzimidazole agarose is able to bind almost all of the applied monoclonal antibody (i.e. giving a yield of 95%) and at the same time give an eluate which is substantially purified. The purity can even be increased by adding substances such as polyvinyl pyrrolidone.

8. Stability at High pH 2-mercapto-benzimidazole was coupled to epichlorohydrin activated 6% agarose beads (Hispanagar) prepared as described in example 1A as well as to divinyl sulfone activated 6% agarose beads (Hispanagar) prepared according to example 1D. Both coupling procedures were according to example 1E.

The contents of 2 mercapto-benzimidazole of the two matrices were determined by elemental analysis and found to be 69 $\mu$mol/g wet (drained) matrix and 42 $\mu$mol/ml wet (drained) matrix respectively.

Both matrices were tested for their stability towards incubation with 1 M sodium hydroxide by following the procedure described below:
Standard Stability Test I) Approximately 1000 mg of the matrix to be tested is washed with 100 ml demineralised water on a sintered glass funnel followed by suction draining for 60 seconds. 500 mg of wet (drained) solid phase matrix is weighed into a 10.0 ml test tube labelled "NaOH" and 9.0 ml 1 M sodium hydroxide is added followed by mixing gently for 1 min. Another 500 mg of wet (drained) solid phase matrix is weighed into a 10 ml test tube labelled "Water" and 9.0 ml water is added followed by gentle mixing for 1 min.

The test tubes are closed tightly with stoppers stored dark at room temperature (20–25° C.) for 7 days.

The matrices are then washed separately with 200 ml water on a sintered glass funnel followed by suction draining for 60 seconds.

II) Each of the solid phases matrices are tested in the "*Standard Immunoglobulin Binding Test*" defined in Example 2.

The stability of the solid phase matrix towards 1 M sodium hydroxide is then calculated and expressed as a percentage compared to the control which has only been incubated in water according to the following formula:

Stability=(percentage bound of NaOH treated matrix/percentage bound of control)×100%

Results

| Solid phase matrix | Stability, % |
|---|---|
| 2-mercapto-benzimidazole-epichlorohydrin-agarose | 98 |
| 2-mercapto-benzimidazole-divinyl sulfone-agarose | 0 |

The results indicate that matrices produced with divinyl sulfone activated agarose have poor stability in 1M NaOH, whereas epoxy activated agarose gives stable solid phase matrices. It is furthermore demonstrated that 2-mercapto-benzimidazole is a stable ligand in it self.

9. Isolation of Polyclonal Antibodies from Different Species
2-Mercaptobenzoic Acid as the Ligand The following example illustrates the binding efficiency of 2-mercaptobenzoic acid agarose towards polyclonal antibodies from different species, as well as yield and purity of the antibody in the eluate. For the study sera from 5 different species were used.

Polyclonal antibodies: The polyclonal antibodies used originated from normal sera from the following species: goat, horse, rabbit, swine and human. The sera were obtained from freshly drawn blood by mild centrifugation after coagulation for 24 hours at room temperature.

Solid phase matrix: 2-mercaptobenzoic acid agarose was based on epoxy activated 6% agarose beads from Hispanagar and synthesised as described in example 1A and 1E. The ligand concentration was measured by elemental analysis and found to be 65 $\mu$mol/gram wet, but drained matrix.

The solid phase matrix was tested for its polyclonal antibody binding efficiency in a column according to the following procedure:

1) The matrix was washed with water on a sintered glass funnel and finally drained. 1 gram of wet, but drained solid phase matrix was weighed into a small column (inner diameter of 5 mm). The matrix was washed with 5 ml of buffer. (10 mM sodium citrate pH 5.0.). 1 ml of the sample (adjusted to pH 5.0 with 1 M hydrochloric acid) was applied to the column. The column was washed with 20 ml of washing buffer I (1.1 M ammonium sulfate pH 8.0 containing 5 mg/ml sodium 1-octanesulfonate). The column was washed with 5 ml of washing buffer II (1.1 M ammonium sulfate pH 8.0). The matrix was eluted with 10 ml of elution buffer (0.05 M boric acid/NaOH+0.5 M sodium chloride pH 8.6). No pumps were employed in the experiments, all columns were run by gravity (at an approximate flow rate of 0.5–1.0 ml/min).

2) Analyses were performed to determine the relative distribution of immunoglobulin between the non-bound fraction in the run-through after binding, the washing fraction(s) and the eluate. This was done by single radial immunodiffusion (as described in D. Catty and C Raykundalia "Antibodies—a practical approach" Vol I, pp.137–168, 1988) using species specific anti-immunoglobulins as the precipitating antibodies.

The binding capacity was then calculated from the amount of non-bound immunoglobulin present in the run-through and expressed as a percentage of the total amount added to the matrix in the raw material.

The yield was calculated as the percentage of the added immunoglobulin found in the eluate fraction.

The purity of the eluted immunoglobulin was analysed by SDS-PAGE (sodium dodecyl sulfate polyacrylamide electrophoresis) under reducing conditions followed by staining of the protein bands with coomassie brilliant blue. (Precast gel 4–20% tris-glycine, 1 mm cat.no.: EC6025, running 1 hour at 30 mA; tris-glycine SDS running buffer cat.no.: LC2675; tris-glycine sample buffer cat.no.: LC2676; coomassie staining kit LC6025 all chemicals from Novex, USA)

The degree of purity as expressed in percent of the total protein contents was determined by scanning and image processing of the coomassie stained and dried polyacrylamide gel. For this purpose we employed the CREAM system available from Kem-En-Tec A/S, Denmark (cat.no.: 6010+ 6050).

Results

| Serum | binding capacity (%) | Yield (%) | Purity (%) |
|---|---|---|---|
| Goat | 60 | 50 | 60 |
| Swine | 60 | 60 | 70 |
| Rabbit | 80 | 60 | 90 |
| Horse | 60 | 40 | 80 |
| Human | 70 | 60 | 75 |

10. Isolation of IgG from Bovine Serum
2-Mercaptobenzimidazol as the Ligand

The following example illustrates that it is possible to isolate and purify IgG from bovine serum with 2-mercaptobenzimidazol as the ligand.

Bovine serum: The bovine serum used was normal serum. The serum was obtained from freshly drawn blood by mild centrifugation after coagulation for 24 hours at room temperature.

Solid phase matrix: 2-mercaptobenzimidazol agarose was based on epoxy activated 6% agarose beads from Hispanagar and synthesised as described in example 1A and 1E. The ligand concentration was measured by elemental analysis and found to be 69 $\mu$mol/g wet, but drained matrix.

The solid phase matrix was tested for it's polyclonal antibody binding efficiency in a column according to the following procedure:

1) The matrix was washed with water on a sintered glass funnel and finally drained. 2 gram of wet, but drained solid phase matrix is weighed into a small column (inner diameter of 5 mm). The matrix was washed with 5 ml of buffer. (10 mM sodium citrate pH 7.0.). 2 ml of bovine serum was applied to the column. The column was washed with 10 ml of washing buffer (10 mM sodium citrate, 0.25 M NaCl pH 7.0). The matrix was eluted with 20 ml of elution buffer (10 mM sodium citrate pH 3.0). The flow rate was 1.0 ml/min.

2) Analyses were performed to determine the relative distribution of immunoglobulin between the non-bound fraction in the run-through after binding, the washing fraction(s) and the eluate. This was done by single radial immunodiffusion (as described in D. Catty and C Raykundalia "Antibodies—a practical approach" Vol I, pp.137–168, 1988) using rabbit anti cow immunoglobulins (DAKO, Denmark cat.no.: Z247) as the precipitating antibody The binding capacity was then calculated from the amount of non-bound immunoglobulin present in the run-through and expressed as a percentage of the total amount added to the matrix in the raw material.

The yield and purity was determined as described in example 4.
Results

| | |
|---|---|
| Binding capacity | 85% |
| Purity | 80% |
| Yield | 85% |

11. Isolation of Immunoglobulins from Egg Yolk
2-Mercaptobenzimidazol as the Ligand The following example illustrates that it is possible to isolate immunoglobulins from egg yolk with 2-mercaptobenzimidazol as the ligand.

Egg yolk. Egg yolks (from normal chicken eggs) were diluted 1:1 with 0.25 M NaCl. The sample was cenfrifuged in 20 minutes at 10.000 rpm.

Solid phase matrix. 2-mercaptobenzimidazol agarose was based on epoxy activated 6% agarose beads from Hispanagar and synthesised as described in example 1A and 1E. The ligand concentration was measured by elemental analysis and found to be 69 $\mu$mol/gram wet, but drained matrix.

The solid phase matrix was tested for it's efficiency to bind immunoglobulins from egg yolk in a column according to the following procedure:

1) The matrix was washed with water on a sintered glass funnel and finally drained. 0.2 gram of wet, but drained solid phase matrix is weighed into a small column (inner diameter of 5 mm). The matrix was washed with 10 ml of buffer. (10 mM $KH_2PO_4$ 6.1.). 4 ml of the sample was applied to the column. The column was washed with 10 ml washing buffer (10 mM $KH_2PO_4$ 6.1). The matrix was eluted with 16 ml of elution buffer (10 mM sodium citrate pH 3.5).

2) Analyses were performed to determine the relative distribution of immunoglobulin between the non-bound fraction in the run-through after binding, the washing fraction(s) and the eluate. This was done by single radial immunodiffusion (as described in D. Catty and C Raykundalia "Antibodies—a practical approach" Vol I, pp. 137–168, 1988) using rabbit anti chicken IgG (Sigma, USA cat.no.: C-6409) as the precipitating antibody The binding capacity was then calculated from the amount of non-bound immunoglobulin present in the run-through and expressed as a percentage of the total amount added to the matrix in the raw material.

The yield and purity was determined as described in example 4.
Results

| | |
|---|---|
| Binding capacity | 80% |
| Purity | 60% |
| Yield | 80% |

12. Depletion of IgG and Haemoglobin from Fetal Calf Serum

The following example illustrates the efficiency of some of the solid phases according to the invention to deplete IgG and haemoglobin from fetal calf serum. The study was designed to determine the binding efficiency during batch incubation with 14 different solid phases.

Fetal calf serum: The fetal calf serum was obtained from freshly drawn blood by mild centrifugation after coagulation for 24 hours at room temperature.

Solid phase: The following solid phases were used: 2-mercaptobenzimidazol agarose, thiophenol agarose, 4-chlorothiophenol agarose, 2-aminothiophenol agarose, 4-methylmercaptoaniline agarose, 2-mercapto-5-nitrobenzimidazole agarose, benzylmercaptan agarose, 2-chlorophenol agarose, 3-chlorophenol agarose, 4-chlorophenol agarose, 2-mercaptobenzoxazol agarose, 2-mercaptopyridine agarose, 2,5-dimercapto-1,3,4,-thiadiazol agarose, 6-ethoxy-2-mercaptobenzothiazol agarose. All these agaroses were based on epoxy activated 6% agarose beads from Hispanagar and synthesised as described in example 1A and 1E. The ligand concentration was measured for all matrices by elemental analysis and found to be in the range of 60–70 $\mu$mol/g wet, but drained matrix.

The solid phase matrices were tested for their efficiency to deplete IgG and haemoglobin from fetal calf serum according to the following procedure:

1) The matrix was washed with 0.25 M NaCl on a sintered glass funnel and finally drained 0.5 gram of wet, but drained solid phase matrix is weighed into a test tube and added 5 ml of fetal calf serum. The suspension was then incubated on a roller mixer for two hours at room temperature.

2) After incubation the test tube was centrifuged for 5 min. at 2000 RPM to sediment the matrix and a sample of the supernatant was taken out for determination of the amount of IgG left in the serum. This was done by single radial immunodiffusion (as described in D. Catty and C Raykundalia "Antibodies—a practical approach" Vol I, pp.137–168, 1988) using rabbit anti cow immunoglobulins (DAKO, Denmark, cat.no.: Z247) as the precipitating antibody.

3) The concentration of haemoglobin was measured spectrophotometrical at 414 nm. The percentage of haemoglobin left unbound in the serum is calculated as:

$$(Abs_{414\ nm,\ absorbed\ fetal\ calf\ serum}/Abs_{414\ nm,\ fetal\ calf\ serum}) \times 100\%$$

Results

| Sample | % haemoglobin left in serum | % IgG left in serum |
|---|---|---|
| 2-mercaptobenzimidazol agarose | 60 | 30 |
| Thiophenol agarose | 60 | 50 |
| 4-chlorothiophenol agarose | 40 | 40 |
| 2-aminothiophenol agarose | 60 | 30 |
| 4-methylmercaptoaniline agarose | 90 | 60 |
| 2-mercapto-5-nitrobenzimidazole agarose | 30 | 30 |
| Benzylmercaptan agarose | 70 | 60 |
| 2-chlorophenol agarose | 80 | 60 |
| 3-chlorophenol agarose | 70 | 50 |
| 4-chlorophenol agarose | 75 | 50 |
| 2-mercaptobenzoxazol agarose | 75 | 50 |
| 2-mercaptopyridine agarose | 75 | 60 |
| 2,5-dimercapto-1,3,4,-thiadiazol agarose | 10 | 40 |
| 6-ethoxy-2-mercaptobenzothiazol agarose | 60 | 60 |

13. Isolation of Trypsinogen and Chymotrypsinogen from Bovine Pancreas with 2-Mercapto-benzoic Acid Agarose The following example illustrates the use of 2-mercaptobenzoic acid agarose as a suitable matrix for isolation and purification of proteases, e.g. trypsin and chymotrypsin from bovine pancreas.

Pancreas extract: The two proteases were isolated as the proenzymes trypsinogen and chymotrypsinogen from a bovine pancreas extract produced by extraction with sulfuric acid as described, in M. Laskowski, Methods in Enzymology, vol. II, pp 9–10, 1955. After extraction the suspension was adjusted to pH 2.5 by addition of 2 M sodium hydroxide and clarified by filtration and centrifugation for 30 min. at 4000 RPM. Just prior to purification the extract was adjusted to pH 4.5 with 2 M NaOH and centrifugated at 4000 rpm for 5 minutes the supernatant was collected.

Solid phase matrix: 2-mercapto-benzoic acid agarose was based on epichlorohydrin activated 6% agarose beads from Hispanagar and synthesised as described in example 1A and 1E. The ligand concentration was measured by two different methods and found to be 65 μmol/g wet, but drained matrix as determined by elementary analysis and 60 μmol/g as determined by acid-base titration of the immobilised benzoic acid part of the ligand.

The solid phase matrix was tested for the efficiency to bind trypsin and chymotrypsin according to the following procedure:

1) The matrix was washed with water on a sintered glass funnel and finally drained. 2,5 gram of wet, but drained solid phase matrix is weighed into a column (inner diameter of 5 mm). The matrix was washed with 10 ml buffer (10 mM sodium citrate pH 4.5) 50 ml of the extract was applied to the column. The matrix was washed with 15 ml of washing buffer (10 mM sodium citrate pH 4.5). The matrix was eluted with 10 ml elution buffer (50 mM boric acid, 0.5 M NaCl pH 8.7).

2) The purity of the eluate was analysed by SDS-PAGE (sodium dodecyl sulfate polyacrylamide electrophoresis) under reducing conditions followed by staining of the protein bands with coomassie brilliant blue. (Precast gel 4–20% tris-glycine, 1 mm cat.no.:EC6025, running 1 hour at 3 mA; tris-glycine SDS running buffer cat no.: LC2675; tris-glycine sample buffer cat.no.: LC2676; coomassie staining kit LC6025 all chemicals from Novex, USA).

Results

| Total amount of protein in eluate | 65 mg |
|---|---|
| Trypsin in eluate | 35% |
| Chymotrypsin in eluate | 20% |

As can be seen from these results it is surprisingly found that this type of ligand i.e. aromatic ligands comprising an acidic group according to the invention, here represented by 2-mercapto-benzoic acid as the specific ligand, are able to bind very efficiently proteins such as proteases at relatively low pH values and at relatively high ionic strength (i.e. approx 0.25 in ionic strength).

14. Purification of Immunoglobulins from Horse Serum

The following example illustrates the use of 2-mercaptobenzimidazole coupled to agarose beads for purification of immunoglobulins from horse serum. It further illustrates the use of different elution conditions with this type of matrix.

Horse serum: The horse serum was obtained from freshly drawn blood by mild centrifugation after coagulation for 24 hours at room temperature.

Solid phase matrix: 2-mercapto-benzimidazole agarose was produced as described in example 1A and 1E. The ligand concentration was determined to be 69 μmol/g wet but suction drained matrix.

Procedure

1) The matrix was washed with water on a sintered glass funnel and finally drained. 2 g of wet, but drained 2-mercapto-benzimidazole agarose is weighed into a small column (inner diameter of 5 mm). The matrix was washed with 5 ml of 10 mM potassium phosphate, pH 7.0. 2 ml of horse serum adjusted to pH 7.0 with 0.1 M HCl was applied to the column. The column was washed with 10 ml of washing buffer (10 mM potassium phosphate, 0.1 M NaCl, pH 7.0). The matrix was eluted with 20 ml of elution buffer (see below). The flow rate was 1.0 ml/min.

This procedure was followed in three identical experiments except for the use of three different elution buffers:
Elution buffer A=20 mM sodium citrate pH 3.0
Elution buffer B=50 mM ethanol amine/HCl pH 11.0
Elution buffer C=10 mM potassium phosphate pH 7.0+ 30% v/v 1,2-propane diol 2) Analyses were performed to determine the relative distribution of immunoglobulin between the non-bound fraction in the run-through after binding, the washing fraction(s) and the eluate. This was done by single radial immunodiffusion (as described in D. Catty and Raykundalia "Antibodies—a practical approach" Vol I, pp.137–168, 1988) using rabbit anti horse immunoglobulin G (Sigma, USA, cat.no.: H-9015) as the precipitating antibody.

The binding capacity was then calculated from the amount of non-bound immunoglobulin present in the run-through and expressed as a percentage of the total amount added to the matrix in the raw material. The yield and purity was determined as described in example 4.

Results:

|  | Elution buffer A | Elution buffer B | Elution buffer C |
|---|---|---|---|
| Binding capacity % | 85 | 85 | 85 |
| Yield % | 80 | 85 | 80 |
| Purity % | 90 | 90 | 85 |

The results indicated that 2-mercapto-benzimidazole agarose is an efficient solid phase matrix for purification of horse immunoglobulins and that elution may be performed with either weakly acidic or weakly basic buffers or alternatively with a neutral buffer comprising a non-toxic organic solvent such as 1,2-propanediol without compromising yield and purity of the eluted immunoglobulin.

15. Bovine Serum Albumin Binding Efficiency by Different Solid Phase Matrices The following example illustrates the efficiency of different solid phase matrices in a standard binding assay for bovine serum albumin.

Solid phases: A selected range of solid phase matrices were produced on the basis of epichlorohydrin activated agarose beads from Hisapanagar as described in example 1A and 1E. The ligands tested are listed in the table below.

Bovine serum albumin solution pH 4.0 (BSA pH 4.0): Purified bovine serum albumin (Biofac A/S, Denmark) was dissolved to a final concentration of 10 mg/ml in 20 mM sodium citrate pH 4.0+0.2 M sodium chloride.

Bovine serum albumin solution pH 7.0 (BSA pH 7.0): Purified bovine serum albumin (Biofac A/S, Denmark) was dissolved to a final concentration of 10 mg/ml in 20 mM sodium citrate pH 7.0+0.2 M sodium chloride.

Procedure
Standard Albumin Binding Assay

The solid phase matrices were washed with 10 volumes of demineralised water on a vacuum suction filter and drained by gentle suction for 1 min. Two samples of 1.0 g suction drained matrix were then weighed into two 10 ml test tubes followed by the addition of 6.0 ml of BSA pH 4.0 to the first test tube and 6.0 ml BSA pH 7.0 to the second test tube. Two 1.0 g samples of non-derivatised suction drained plain agarose beads from Hispanagar were also added 6.0 ml of the two BSA solutions as negative controls. The test tubes were then close with a stopper and the suspension incubated on a roller mixer for 2 hours at room temperature (20–25° C.). The test tube was then centrifuged for 5 min. at 2000 RPM in order to sediment the matrix. The supernatants were then isolated from the solid phase matrix by pipetting into a separate test tubes, avoiding the carry-over of any matrix particles and filtered through a small non-adsorbing 0.2 µm filter (Millipore, USA). Following this a determination of the concentration of non-bound BSA in the supernatant is performed by measuring the optical density (OD) at 280 nm on a spectrophotometer.

The amount of BSA bound to the matrices were then calculated according to the following formula:

mg BSA bound per g suction drained matrix=(1-($OD$ of test supernatant/$OD$ of control))×60

The precision of this method is better than +/−5%.

Results

The table gives the amount of BSA bound in mg per gram wet, but suction drained matrix as a function of the coupled ligand and the pH of the BSA solution.

| Ligand coupled to solid phase matrix | BSA pH 4.0 | BSA pH 7.0 |
|---|---|---|
| 3-hydroxy-benzoic acid | 22 | 0 |
| 4-hydroxy-benzoic acid | 5 | 0 |
| 3,5-dihydroxy-benzoic acid | 36 | 58 |
| 2,4-dihydroxy-benzoic acid | 41 | 0 |
| 2-hydroxy-1-naphthalic acid | 58 | 0 |
| 3-amino-benzoic acid | 56 | 0 |
| 2-amino-benzoic acid | 51 | 0 |
| 4-amino-benzoic acid | 59 | 0 |
| 3,4-di-amino-benzoic acid | 9 | 0 |
| 5-amino-iso-phthalic acid | 17 | 51 |
| 1-amino-2-naphthol-4-sulfonic acid | 21 | 52 |
| p-coumaric acid | 26 | 0 |
| 2-mercapto-benzoic acid | 59 | 0 |
| 2-mercapto-nicotinic acid | 30 | 0 |
| 5-mercapto-1-tetrazol-acetic acid | 26 | 0 |
| 3-amino-1,2,4-triazol-5-carboxylic acid | 6 | 30 |
| 2,5-di-mercapto-1,3,4-thiadiazol | 0 | 20 |
| 2-amino-6-nitro-benzothiazol | 28 | 46 |
| 2-mercaptobenzthiazol | 42 | 45 |
| Sulfa-thiazol | 28 | 0 |
| Sulfa-methizol | 20 | 0 |
| 2-amino-pyridin | 0 | 0 |
| 2-mercapto-pyridin | 8 | 26 |
| 2-hydroxy-pyridin | 0 | 19 |
| 2-mercapto-5-nitro-benzimidazol | 58 | 47 |

What is claimed is:

1. A method for the isolation of proteins from a solution containing one or more of proteins, comprising the following operations:
   a) contacting a solution containing one or more proteins having a pH in the range of 2.5 to 5.5 and a total salt content corresponding to an ionic strength of at the most 2.0 with a solid phase matrix comprising a functionalised matrix backbone carrying a plurality of functional groups of the following formula

M-SP1-X-A-SP2-ACID wherein M designates the matrix backbone and SP1-X-A-SP2-ACID designates a ligand -L; SP1 designates a spacer which is not a divinyl sulfone derived spacer; X designates —O—, —S—, or —NH—; A designates a mono- or bicyclic optionally substituted aromatic or heteroaromatic moiety; SP2 designates an optional spacer; and ACID designates an acidic group;
   with the proviso that the molecular weight of the ligand -L is at the most 500 Dalton;
   whereby at least a part of the proteins becomes bound to the solid phase matrix;
   b) separating the solid phase matrix having proteins bound thereto from the solution;
   c) optionally washing the solid phase matrix; and
   d) contacting the solid phase matrix with an eluent in order to liberate one or more of the proteins from the solid phase matrix, wherein the eluent used comprises less than 10% (v/v) of organic solvents.

2. A method according to claim 1, wherein ligand concentration is in the range of 1–130 μmol/g wet, but suction drained solid phase matrix.

3. A method according to claim 1, wherein A is selected from benzene radicals and naphthalene radicals.

4. A Method according to claim 1, wherein A is a hetero-aromatic moiety selected from monocyclic hetero-aromatic radicals selected from thiophene, furan, pyran, pyrrole, imidazole, pyrazole, isothiazole, isoxazole, pyridine, pyrazine, pyrimidine, and pyridazine radicals; and bicyclic heteroaromatic radicals selected from indole, purine, quinoline, benzofuran, benzimidazole, benzothiazole, and benzoxazole radicals.

5. A method according to claim 4, wherein A is selected from radicals of pyridine, benzimidazole, benzo-thiazole, and benzoxazole radicals.

6. A method according to claim 1, wherein the acidic group is selected from a carboxylic acid group (—COOH), a sulfonic acid group (—$SO_2OH$), sulfinic acid group (—S(O)OH), phosphinic acid group (—PH(O)(OH)), phosphonic acid monoester groups (—P(O)(OH)(OR)), and phosphonic acid group (—P(O)(OH)$_2$).

7. A method according to claim 1, wherein SP2 designates $C_{1-6}$-alkylene, $C_{2-6}$-alkenylene, or a single bond.

8. A method according to claim 1, wherein the ligand L is derived from compounds selected from dihydroxy-beazoic acids; amino-benzoic acids; diamino-benzoic acids; mercapto-benzoic acids; mercapto-nicotinic acids; mercapto-tetrazole acetic acids; benzimidazoles; benzothiazoles; beuzoxazoles; and diacids.

9. A method according to claim 8, wherein the ligand is derived from compounds selected from 2,5-dihydroxy-benzoic acid, 2-amino-benzoic acid, 3-amino-benzoic acid, 4-amino-benzoic acid, 2-mercapto-benzoic acid, 2-mercapto-nicotinic acid, 5-mercapto-1-tetrazole acetic acid, 2-mercapto-benzimidazole, 4-aminophthalic acid, and 5-aminoisophthalic acid.

10. A method according to claim 1, wherein all of the -SP1-X-A-SP2-ACID units are substantially identical.

11. A method according to claim 1, wherein the total salt content of the solution containing the proteins corresponds to an ionic strength in the range of 0.05 to 2.0.

12. A method according to claim 1, wherein the solution containing the proteins comprises lyotropic salts in a concentration of at the most 0.4 M.

13. A method according to claim 1, wherein the pH of the eluent is in the range of 6.0 to 11.

14. A method according to claim 1, wherein the eluent used (operation (d)) comprises less than 5% (v/v) of organic solvents.

15. A method according to claim 1, wherein the washing of the solid phase matrix (operation (c)) comprises washing with an aqueous solution comprising a negatively charged detergent.

16. A method according to claim 15, wherein the washing of the solid phase matrix (operation (c)) comprises washing with an inorganic or organic salt buffer comprising a negatively charged detergent.

17. A method according to claim 1, wherein the solution containing the proteins comprises a negatively charged detergent.

* * * * *